United States Patent
Scheller et al.

(10) Patent No.: US 9,549,853 B2
(45) Date of Patent: *Jan. 24, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/956,764

(22) Filed: Dec. 2, 2015

(65) Prior Publication Data

US 2016/0081854 A1    Mar. 24, 2016

Related U.S. Application Data

(63) Continuation of application No. 13/961,952, filed on Aug. 8, 2013, now Pat. No. 9,232,975.

(51) Int. Cl.
| | |
|---|---|
| *A61B 18/18* | (2006.01) |
| *A61F 9/008* | (2006.01) |
| *A61B 18/22* | (2006.01) |
| *A61B 18/00* | (2006.01) |
| *A61B 18/20* | (2006.01) |

(52) U.S. Cl.
CPC .......... *A61F 9/00821* (2013.01); *A61B 18/22* (2013.01); *A61B 2018/00589* (2013.01); *A61B 2018/00595* (2013.01); *A61B 2018/202* (2013.01); *A61B 2018/209* (2013.01); *A61B 2018/2238* (2013.01); *A61F 2009/00863* (2013.01)

(58) Field of Classification Search
CPC ............................ A61F 9/00821; A61F 9/008
USPC ........................................................ 606/4, 16
See application file for complete search history.

(56) References Cited

U.S. PATENT DOCUMENTS

| | | |
|---|---|---|
| 5,190,050 A | 3/1993 | Nitzsche |
| 5,355,871 A | 10/1994 | Hurley et al. |
| 5,381,782 A | 1/1995 | DeLaRama et al. |

(Continued)

FOREIGN PATENT DOCUMENTS

| | | |
|---|---|---|
| EP | 0900547 B1 | 3/1999 |
| NL | WO 2013/133717 | 9/2013 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include an actuation structure, a nosecone fixed to the actuation structure by one or more links and one or more link pins, a housing tube having a first housing tube portion with a first stiffness and a second housing tube portion with a second stiffness, and an optic fiber disposed in the housing tube and the actuation structure. A compression of the actuation structure may be configured to gradually curve the housing tube and the optic fiber. A decompression of the actuation structure may be configured to gradually straighten the housing tube and the optic fiber.

20 Claims, 28 Drawing Sheets

(56) References Cited

U.S. PATENT DOCUMENTS

| | | |
|---|---|---|
| 5,439,000 A | 8/1995 | Gunderson et al. |
| 5,454,794 A | 10/1995 | Narciso et al. |
| 5,520,222 A | 5/1996 | Chikama |
| 5,855,577 A | 1/1999 | Murphy-Chutorian et al. |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 * | 3/2005 | Sonnenschein ...... A61B 1/0005 227/175.1 |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | McGowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 9,232,975 B2 * | 1/2016 | Scheller .............. A61F 9/00821 |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeny et al. |
| 2005/0277874 A1 | 12/2005 | Selkee |
| 2006/0129175 A1 | 6/2006 | Griffin et al. |
| 2006/0178674 A1 | 8/2006 | McIntyre |
| 2007/0185514 A1 | 8/2007 | Kirchhevel |
| 2007/0260231 A1 | 11/2007 | Rose et al. |
| 2008/0132761 A1 | 6/2008 | Sonnenschein et al. |
| 2009/0018393 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0191224 A1 | 7/2010 | Butcher |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |

* cited by examiner

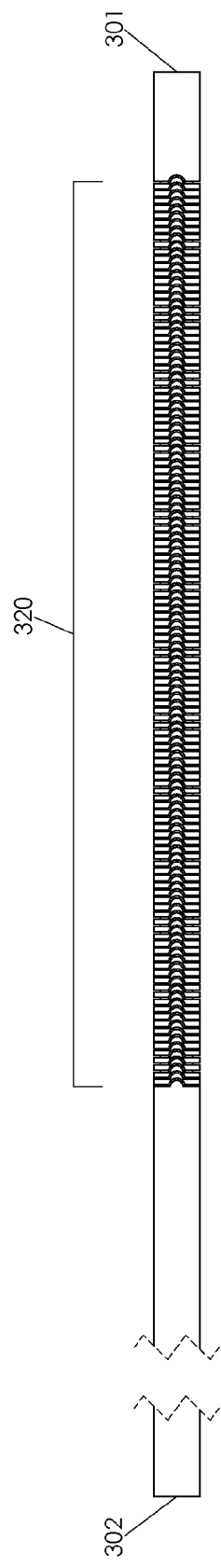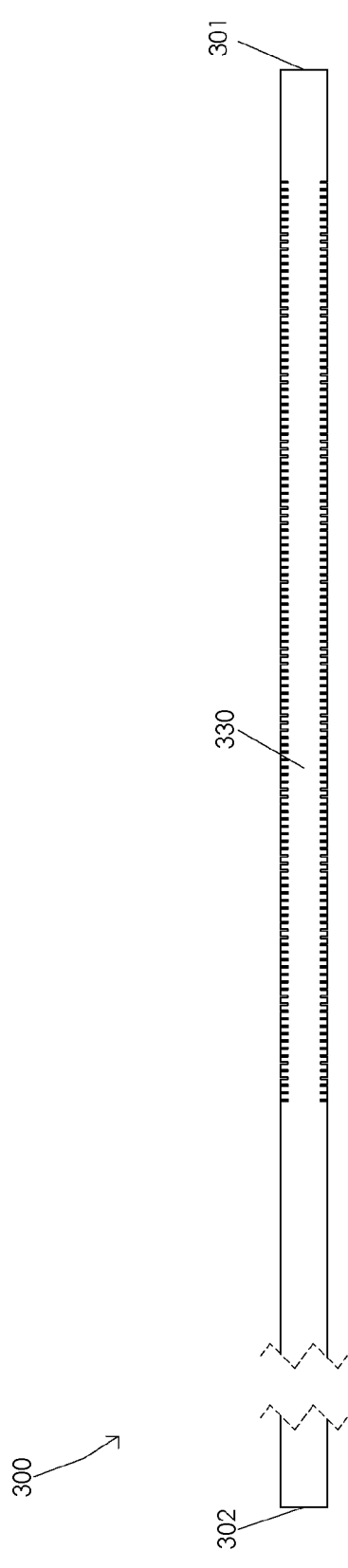

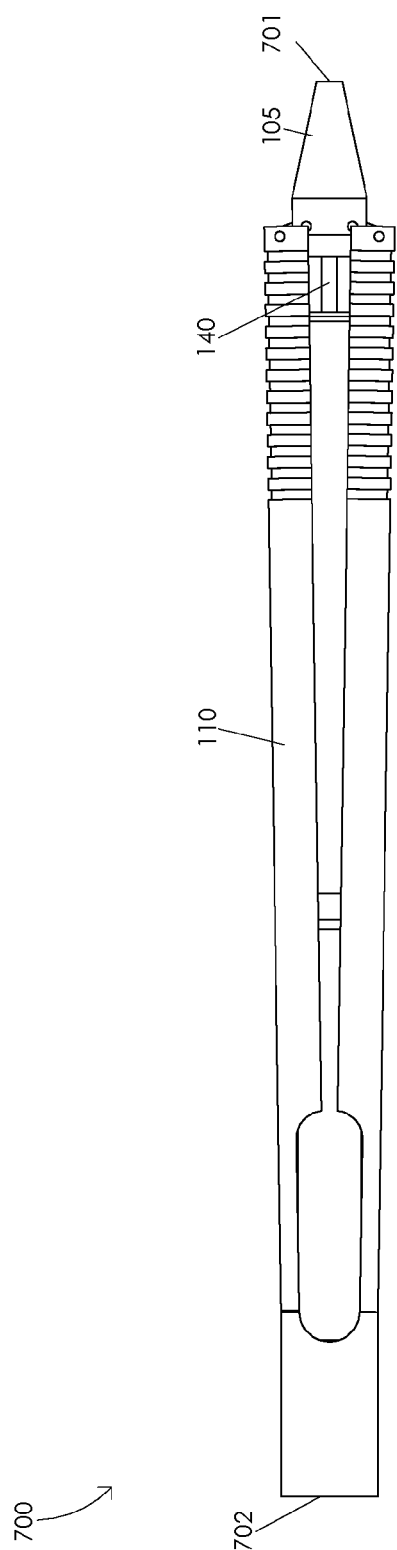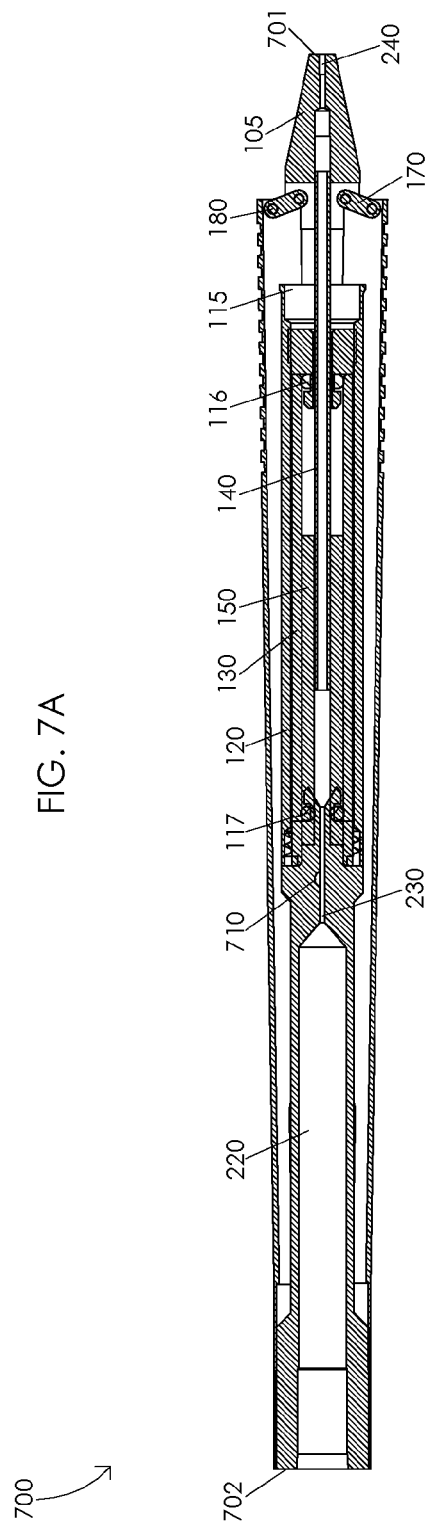
FIG. 7A
FIG. 7B

US 9,549,853 B2

STEERABLE LASER PROBE

CROSS-REFERENCE TO RELATED APPLICATIONS

This Application is a continuation of prior application Ser. No. 13/961,952 filed Aug. 8, 2013.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. Illustratively, a steerable laser probe may comprise an actuation structure, a nosecone fixed to the actuation structure by one or more links and one or more link pins, a housing tube having a first housing tube portion with a first stiffness and a second housing tube portion with a second stiffness, and an optic fiber disposed in the housing tube and the actuation structure. In one or more embodiments, a compression of the actuation structure may be configured to gradually curve the housing tube. Illustratively, a gradual curving of the housing tube may be configured to gradually curve the optic fiber. In one or more embodiments, a demo compression of the actuation structure may be configured to gradually straighten the housing tube. Illustratively, a gradual straightening of the housing tube may be configured to gradually curve the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 3A, 3B, and 3C are schematic diagrams illustrating a housing tube;

FIGS. 7A and 7B are schematic diagrams illustrating a handle;

DETAILED DESCRIPTION OF AN ILLUSTRATIVE EMBODIMENT

Figure 1:
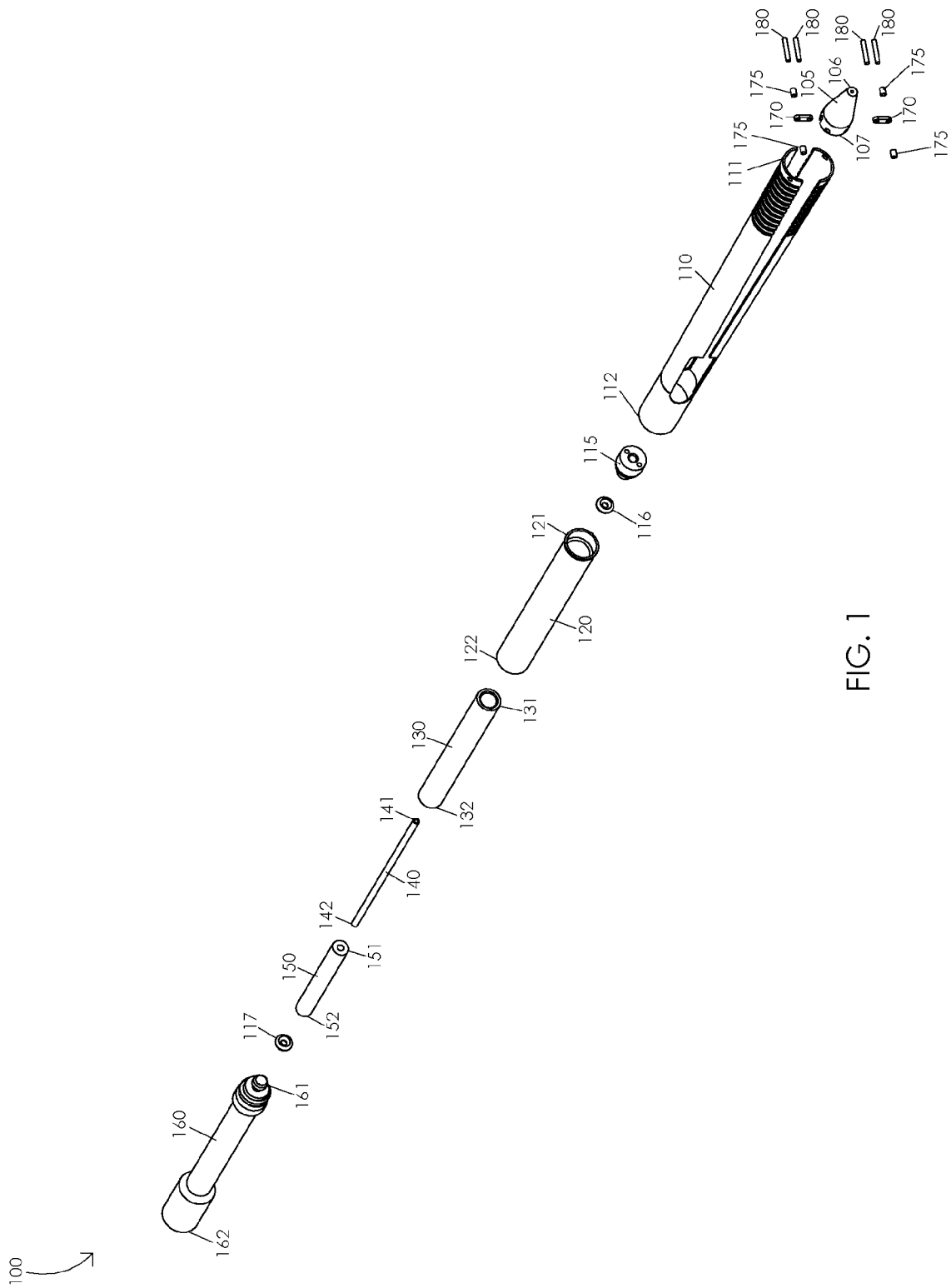
FIG. 1 is a schematic diagram illustrating an exploded view of a handle assembly.

FIG. 1 is a schematic diagram illustrating an exploded view of a handle assembly 100. Illustratively, a handle assembly 100 may comprise a nosecone 105 having a nosecone distal end 106 and a nosecone proximal end 107, an actuation structure 110 having an actuation structure distal end 111 and an actuation structure proximal end 112, a front plug 115, a distal ring 116, a proximal ring 117, an outer sleeve 120 having an outer sleeve distal end 121 and an outer sleeve proximal end 122, an actuation guide 130 having an actuation guide distal end 131 and an actuation guide proximal end 132, an inner hypodermic tube 140 having an inner hypodermic tube distal end 141 and an inner hypodermic tube proximal end 142, a piston 150 having a piston distal end 151 and a piston proximal end 152, an end plug 160 having an end plug distal end 161 and an end plug proximal end 162, one or more links 170, one or more spacers 175, and one or more link pins 180. In one or more embodiments, nosecone 105, actuation structure 110, front plug 115, outer sleeve 120, actuation guide 130, inner hypodermic tube 140, piston 150, and end plug 160 may be manufactured from any suitable material, e.g., polymers, metals, metal alloys, etc., or from any combination of suitable materials.

Figure 2A:
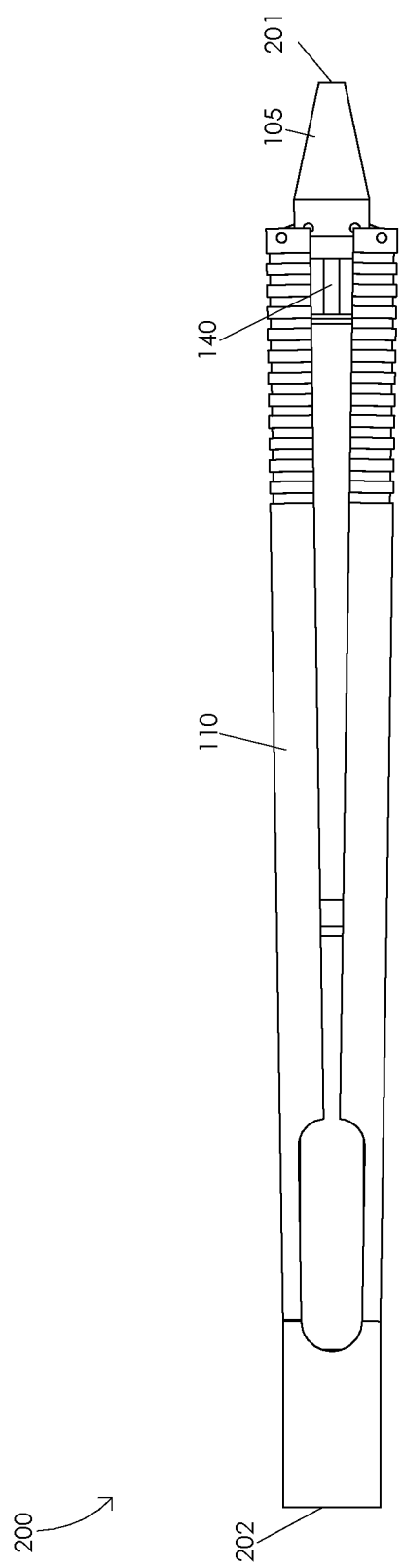
FIGS. 2A and 2B are schematic diagrams illustrating a handle.
Figure 2B:
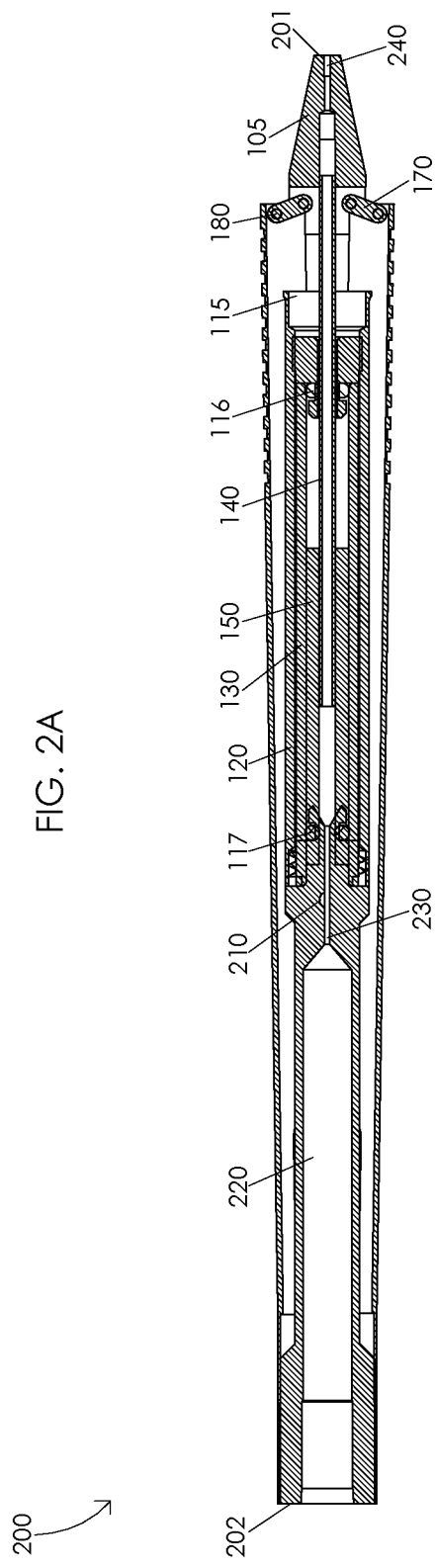

FIGS. 2A and 2B are schematic diagrams illustrating a handle 200. FIG. 2A illustrates a side view of a handle 200. Illustratively, handle 200 may comprise a handle distal end 201 and a handle proximal end 202. In one or more embodiments, a portion of nosecone 105 may be fixed to a portion of actuation structure 110, e.g., nosecone proximal end 107 may be fixed to actuation structure distal end 111. Illustratively, nosecone 105 may be fixed to actuation structure 110, e.g., by one or more links 170. In one or more embodiments, one or more link pins 180 may be configured to fix nosecone 105 to one or more links 170, e.g., a particular link pin 180 may be disposed within nosecone 105 and a particular link 170. Illustratively, one or more link pins 180 may be configured to fix actuation structure 110 to one or more links 170, e.g., a particular link pin 180 may be disposed within actuation structure 110 and a particular link 170. In one or more embodiments, a first link pin 180 may be configured to fix nosecone 105 to a particular link 170 and a second link pin 180 may be configured to fix actuation structure 110 to the particular link 175. Illustratively, one or more spacers 175 may be configured to prevent undesirable movement of one or more links 170 relative to one or more link pins 180, e.g., a particular spacer 175 may be disposed over a portion of a particular link pin 180 extending from a particular link 170.

In one or more embodiments, a portion of inner hypodermic tube 140 may be disposed within piston 150, e.g., inner hypodermic tube proximal end 142 may be disposed within piston 150. Illustratively, a portion of inner hypodermic tube 140 may be fixed within piston 150, e.g., by an adhesive or any suitable fixation means. In one or more embodiments, inner hypodermic tube proximal end 142 may be fixed within piston 150, e.g., by an adhesive or any suitable fixation means. Illustratively, actuation guide 130 may be disposed within outer sleeve 120. In one or more embodiments, actuation guide 130 may be fixed within outer sleeve 120, e.g., by an adhesive or any suitable fixation means. Illustratively, piston 150 may be disposed within actuation guide 130. In one or more embodiments, piston 150 may be configured to actuate within actuation guide 130.

In one or more embodiments, distal ring 116 may be disposed over a portion of front plug 115. Illustratively, front plug 115 may be configured to interface with a portion of outer sleeve 120, e.g., front plug 115 may be configured to interface with outer sleeve distal end 121. In one or more embodiments, front plug 115 may be configured to interface with a portion of actuation guide 130, e.g., front plug 115 may be configured to interface with actuation guide distal end 131. Illustratively, front plug 115 may be disposed within outer sleeve 120. In one or more embodiments, a portion of front plug 115 may be disposed within actuation guide 130. Illustratively, distal ring 116 may be disposed within actuation guide 130, e.g., distal ring 116 may be configured to form a hermetic seal within actuation guide 130.

In one or more embodiments, proximal ring 117 may be disposed over a portion of end plug 160. Illustratively, end plug 160 may be configured to interface with a portion of outer sleeve 120, e.g., end plug 160 may be configured to interface with outer sleeve proximal end 122. In one or more embodiments, end plug 160 may be configured to interface with a portion of actuation guide 130, e.g., end plug 160 may be configured to interface with actuation guide proximal end 132. For example, a portion of end plug 160 may be disposed within actuation guide 130. Illustratively, proximal ring 117 may be disposed within actuation guide 130, e.g., proximal ring 117 may be configured to form a hermetic seal within actuation guide 130. In one or more embodiments, end plug 160 may be disposed within outer sleeve 120. Illustratively, inner hypodermic tube 140 may be disposed within piston 150, actuation guide 130, front plug 115, distal ring 116, and nosecone 105. In one or more embodiments, a portion of inner hypodermic tube 140 may be fixed within nosecone 105, e.g., inner hypodermic tube distal end 141 may be fixed within nosecone 105. Illustratively, a portion of inner hypodermic tube 140 may be fixed within nosecone 105, e.g., by an adhesive or any suitable fixation means.

In one or more embodiments, a compression of actuation structure 110 may be configured to rotate one or more links 170 about one or more link pins 180. Illustratively, a rotation of one or more links 170 about one or more link pins 180 may be configured to extend a particular link pin 180, e.g., a particular link pin 180 disposed in nosecone 105, relative to handle proximal end 202. In one or more embodiments, an extension of a particular link pin 180 disposed in nosecone 105 relative to handle proximal end 202 may be configured to extend nosecone 105 relative to handle proximal end 202. Illustratively, a compression of actuation structure 110 may be configured to extend nosecone 105 relative to handle proximal end 202. In one or more embodiments, an extension of nosecone 105 relative to handle proximal end 202 may be configured to extend inner hypodermic tube 140 relative to handle proximal end 202. Illustratively, an extension of inner hypodermic tube 140 relative to handle proximal end 202 may be configured to actuate piston 150 within actuation guide 130. In one or more embodiments, a compression of actuation structure 110 may be configured to extend piston 150 relative to handle proximal end 202.

In one or more embodiments, a decompression of action structure 110 may be configured to rotate one or more links 170 about one or more link pins 180. Illustratively, a rotation of one or more links 170 about one or more link pins 180 may be configured to retract a particular link pin 180, e.g., a particular link pin 180 disposed in nosecone 105, relative to handle proximal end 202. In one or more embodiments, a retraction of a particular link pin 180 disposed in nosecone 105 relative to handle proximal end 202 may be configured to retract nosecone 105 relative to handle proximal end 202. Illustratively, a decompression of actuation structure 110 may be configured to retract nosecone 105 relative to handle proximal end 202. In one or more embodiments, a retraction of nosecone 105 relative to handle proximal end 202 may be configured to retract inner hypodermic tube 140 relative to handle proximal end 202. Illustratively, a retraction of inner hypodermic tube 140 relative to handle proximal end 202 may be configured to actuate piston 150 within actuation guide 130. In one or more embodiments, a decompression of actuation structure 110 may be configured to retract piston 150 relative to handle proximal end 202.

FIG. 2B illustrates a cross-sectional view of a handle 200. In one or more embodiments, handle 200 may comprise an optic fiber housing 210, an inner bore 220, an optic fiber guide 230, and a housing tube housing 240. Illustratively, handle 200 may be manufactured from any suitable material, e.g., polymers, metals, metal alloys, etc., or from any combination of suitable materials.

Figure 3C:
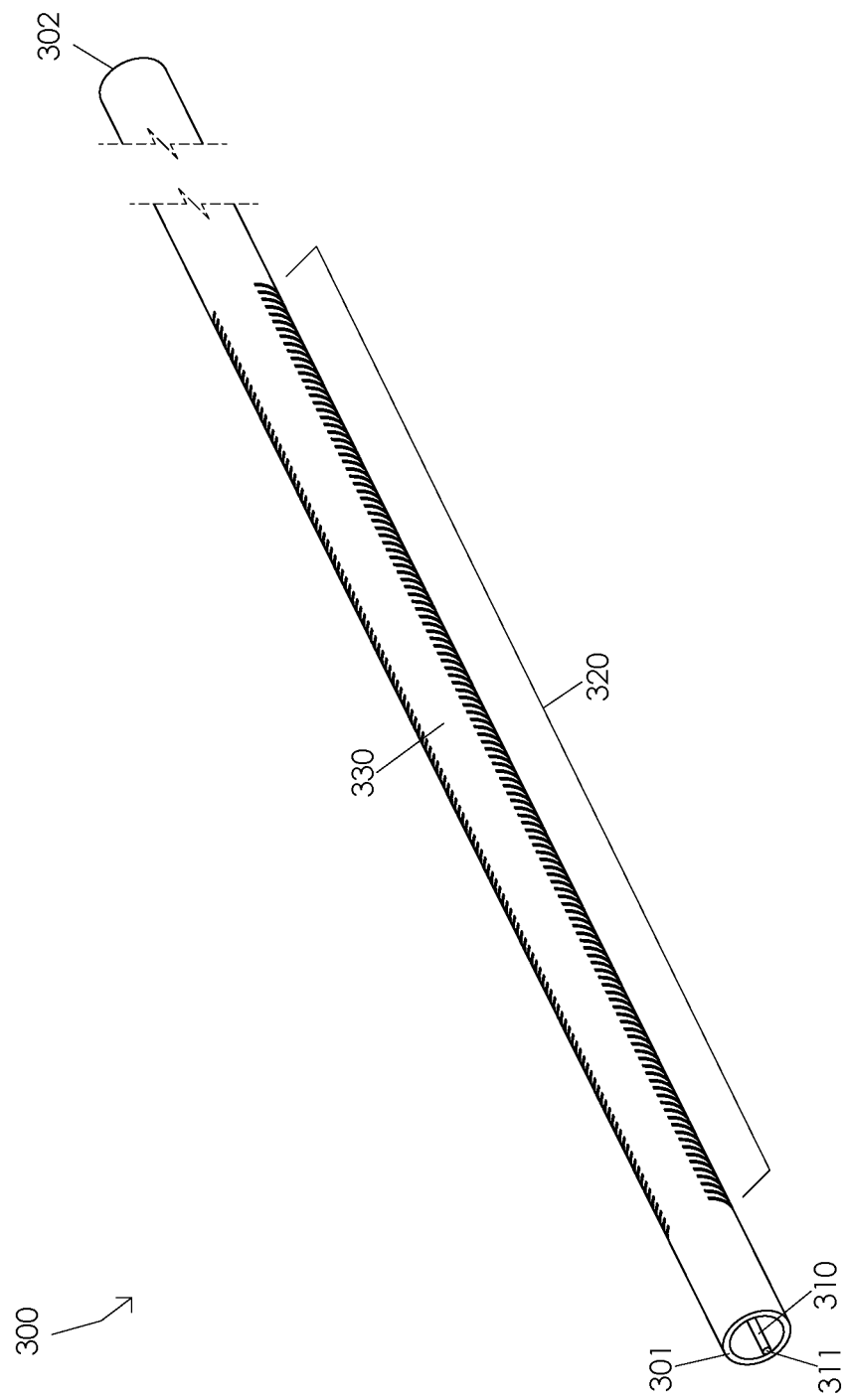

FIGS. 3A, 3B, and 3C are schematic diagrams illustrating a housing tube 300. In one or more embodiments, housing tube 300 may comprise a housing tube distal end 301 and a housing tube proximal end 302. Housing tube 300 may be manufactured from any suitable material, e.g., polymers, metals, metal alloys, etc., or from any combination of suitable materials. Illustratively, housing tube 300 may be manufactured with dimensions configured for microsurgical procedures. FIG. 3A illustrates a housing tube 300 oriented to illustrate a first housing tube portion 320. Illustratively, first housing tube portion 320 may have a first stiffness. FIG. 3B illustrates a housing tube 300 oriented to illustrate a second housing tube portion 330. Illustratively, second housing tube portion 330 may have a second stiffness. In one or more embodiments, the second stiffness may be greater than the first stiffness. Illustratively, first housing tube portion 320 may comprise a first material having a first stiffness. In one or more embodiments, second housing tube portion 330 may comprise a second material having a second stiffness. Illustratively, the second stiffness may be greater than the first stiffness.

In one or more embodiments, housing tube 300 may comprise a non-uniform inner diameter or a non-uniform outer diameter, e.g., to vary a stiffness of one or more portions of housing tube 300. Illustratively, a first housing tube portion 320 may comprise a first inner diameter of housing tube 300 and a second housing tube portion 330 may comprise a second inner diameter of housing tube 300. In one or more embodiments, the first inner diameter of housing tube 300 may be larger than the second inner diameter of housing tube 300. Illustratively, a first housing tube portion 320 may comprise a first outer diameter of housing tube 300 and a second housing tube portion 330 may comprise a second outer diameter of housing tube 300. In one or more embodiments, the first outer diameter of housing tube 300 may be smaller than the second outer diameter of housing tube 300.

In one or more embodiments, first housing tube portion 320 may comprise one or more apertures configured to produce a first stiffness of first housing tube portion 320. Illustratively, second housing tube portion 330 may comprise a solid portion of housing tube 300 having a second stiffness. In one or more embodiments, the second stiffness may be greater than the first stiffness. Illustratively, first housing tube portion 320 may comprise one or more apertures configured to produce a first stiffness of first housing tube portion 320. In one or more embodiments, second housing tube portion 330 may comprise one or more apertures configured to produce a second stiffness of second housing tube portion 330. Illustratively, the second stiffness may be greater than the first stiffness.

In one or more embodiments, first housing tube portion 320 may comprise a plurality of slits configured to separate one or more solid portions of housing tube 300. Illustratively, a plurality of slits may be cut, e.g., laser cut, into first housing tube portion 320. In one or more embodiments, first housing tube portion 320 may comprise a plurality of slits configured to minimize a force of friction between housing tube 300 and a cannula, e.g., as housing tube 300 is inserted into the cannula or as housing tube 300 is extracted from the cannula. For example, each slit of the plurality of slits may comprise one or more arches configured to minimize a force of friction between housing tube 300 and a cannula.

FIG. 3C illustrates an angled view of housing tube 300. Illustratively, an optic fiber 310 may be disposed within housing tube 300. In one or more embodiments, optic fiber 310 may comprise an optic fiber distal end 311 and an optic fiber proximal end 312. Illustratively, optic fiber 300 may be configured to transmit light, e.g., laser light, illumination light, etc. In one or more embodiments, optic fiber 310 may be disposed within housing tube 300 wherein optic fiber distal end 311 may be adjacent to housing tube distal end 301. Illustratively, optic fiber 310 may be disposed within housing tube 300 wherein a portion of optic fiber 310 may be adjacent to a portion of first housing tube portion 320. In one or more embodiments, a portion of optic fiber 310 may be fixed to an inner portion of housing tube 300, e.g., by an adhesive or any suitable fixation means.

Figure 4:
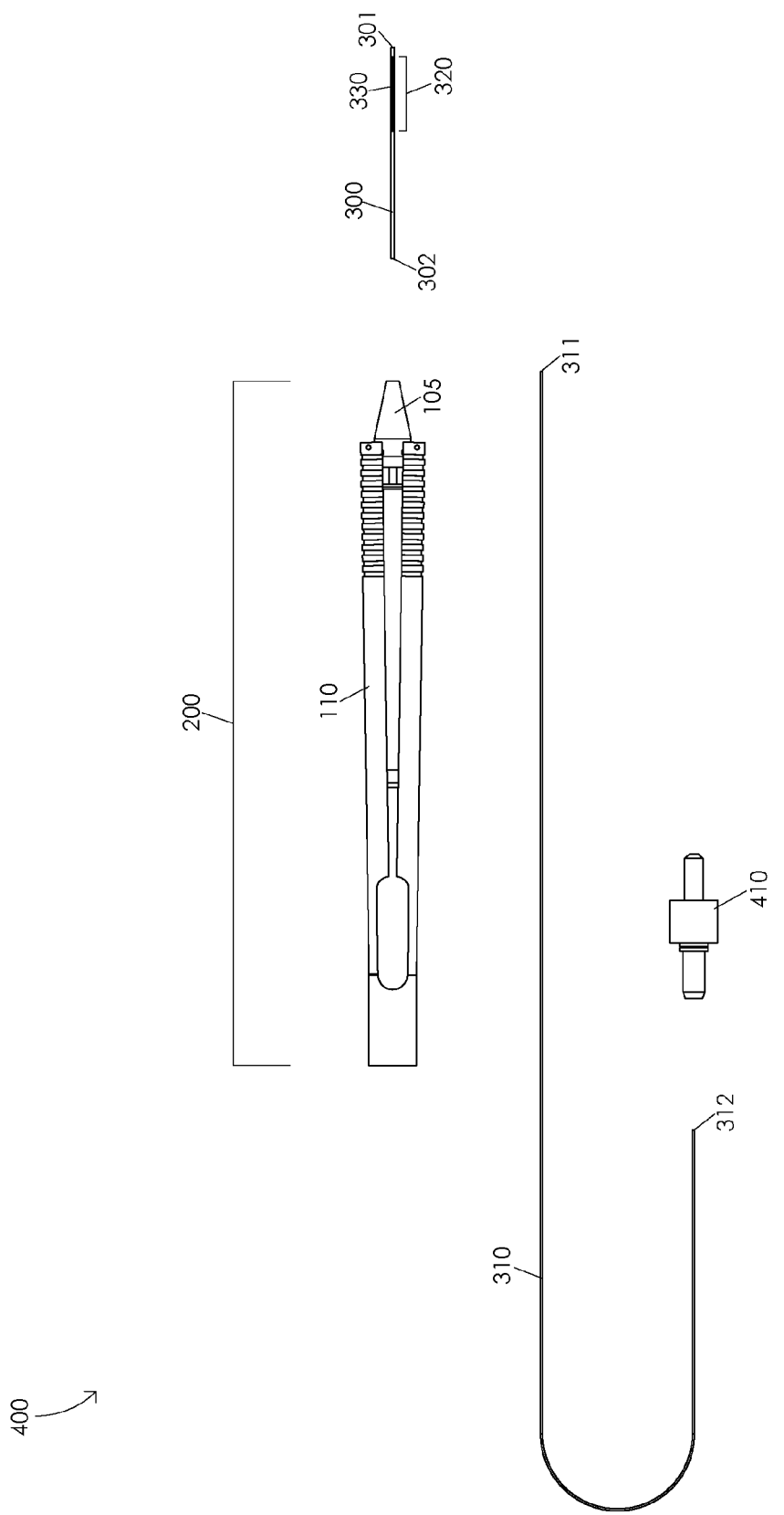
FIG. 4 is a schematic diagram illustrating an exploded view of a steerable laser probe assembly.

FIG. 4 is a schematic diagram illustrating an exploded view of a steerable laser probe assembly 400. In one or more embodiments, a steerable laser probe assembly 400 may comprise a handle 200, a housing tube 300 having a housing tube distal end 301 and a housing tube proximal end 302, an optic fiber 310 having an optic fiber distal end 311 and an optic fiber proximal end 312, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of housing tube 300 may be fixed to nosecone 105, e.g., housing tube proximal end 302 may be fixed to nosecone distal end 106. In one or more embodiments, a portion of housing tube 300 may be fixed to nosecone 105, e.g., by an adhesive or any suitable fixation means. Illustratively, a portion of housing tube 300 may be disposed within nosecone 105, e.g., housing tube proximal end 302 may be disposed within nosecone 105. In one or more embodiments, a portion of housing tube 300 may be fixed within nosecone 105, e.g., by an adhesive or any suitable fixation means. Illustratively, a portion of housing tube 300 may be disposed within housing tube housing 240, e.g., housing tube proximal end 302 may be disposed within housing tube housing 240. In one or more embodiments, a portion of housing tube 300 may be fixed within housing tube housing 240, e.g., by an adhesive or any suitable fixation means. For example, a portion of housing tube 300 may be fixed within housing tube housing 240 by a press fit, a weld, etc.

Illustratively, optic fiber 310 may be disposed within inner bore 220, optic fiber guide 230, optic fiber housing 210, piston 150, inner hypodermic tube 140, nosecone 105, and housing tube 300. In one or more embodiments, optic fiber 310 may be disposed within housing tube 300 wherein optic fiber distal end 311 is adjacent to housing tube distal end 301. Illustratively, optic fiber 310 may be disposed within housing tube 300 wherein a portion of optic fiber 310 is adjacent to first housing tube portion 320. In one or more embodiments, a portion of optic fiber 310 may be fixed to a portion of housing tube 300, e.g., by an adhesive or any suitable fixation means. Illustratively, a portion of optic fiber 310 may be fixed in a position relative to handle proximal end 202. In one or more embodiments, optic fiber 310 may be fixed within optic fiber housing 210, e.g., by an adhesive or any suitable fixation means. For example, optic fiber 310 may be fixed within optic fiber housing 210 by a press fit, a setscrew, etc. Illustratively, a first portion of optic fiber 310 may be fixed in optic fiber housing 210 and a second portion of optic fiber 310 may be fixed to a portion of housing tube 300.

In one or more embodiments, a compression of actuation structure 110 may be configured to rotate one or more links 170 about one or more link pins 180. Illustratively, a rotation of one or more links 170 about one or more link pins 180 may be configured to extend nosecone 105 relative to handle proximal end 202. In one or more embodiments, an extension of nosecone 105 relative to handle proximal end 202 may be configured to extend housing tube 300 relative to handle proximal end 202. Illustratively, an extension of housing tube 300 relative to handle proximal end 202 may be configured to extend housing tube 300 relative to optic fiber 310. In one or more embodiments, a portion of optic fiber 310, e.g., a portion of optic fiber 310 fixed to housing tube 300, may be configured to resist an extension of housing tube 300 relative to optic fiber 310. Illustratively, optic fiber 310 may be fixed within optic fiber housing 210 and optic fiber 310 may be fixed to housing tube 300. In one or more embodiments, an extension of housing tube 300 relative to optic fiber 310 may be configured to apply a force to a portion of housing tube 300. Illustratively, an application of a force to a portion of housing tube 300 may be configured to compress a portion of housing tube 300, e.g., an application of a force to a portion of housing tube 300 may be configured to compress first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310. In one or more embodiments, a compression of actuation structure 110 may be configured to gradually curve optic fiber 310. Illustratively, a compression of actuation structure 110 may be configured to gradually curve housing tube 300.

In one or more embodiments, a decompression of actuation structure 110 may be configured to rotate one or more links 170 about one or more link pins 180. Illustratively, a rotation of one or more links 170 about one or more link pins 180 may be configured to retract nosecone 105 relative to handle proximal end 202. In one or more embodiments, a refraction of nosecone 105 relative to handle proximal end 202 may be configured to retract housing tube 300 relative to handle proximal end 202. Illustratively, a retraction of housing tube 300 relative to handle proximal end 202 may be configured to retract housing tube 300 relative to optic fiber 310. In one or more embodiments, a portion of optic fiber 310, e.g., a portion of optic fiber 310 fixed to housing tube 300, may be configured to facilitate a retraction of housing tube 300 relative to optic fiber 310. Illustratively, optic fiber 310 may be fixed within optic fiber housing 210 and optic fiber 310 may be fixed to housing tube 300. In one or more embodiments, a retraction of housing tube 300 relative to optic fiber 310 may be configured to reduce a force applied to a portion of housing tube 300. Illustratively, a reduction of a force applied to a portion of housing tube 300 may be configured to decompress a portion of housing tube 300, e.g., a reduction of a force applied to a portion of housing tube 300 may be configured to decompress first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310. In one or more embodiments, a decompression of actuation structure 110 may be configured to gradually straighten optic fiber 310. Illustratively, a decompression of actuation structure 110 may be configured to gradually straighten housing tube 300.

Figure 5A:
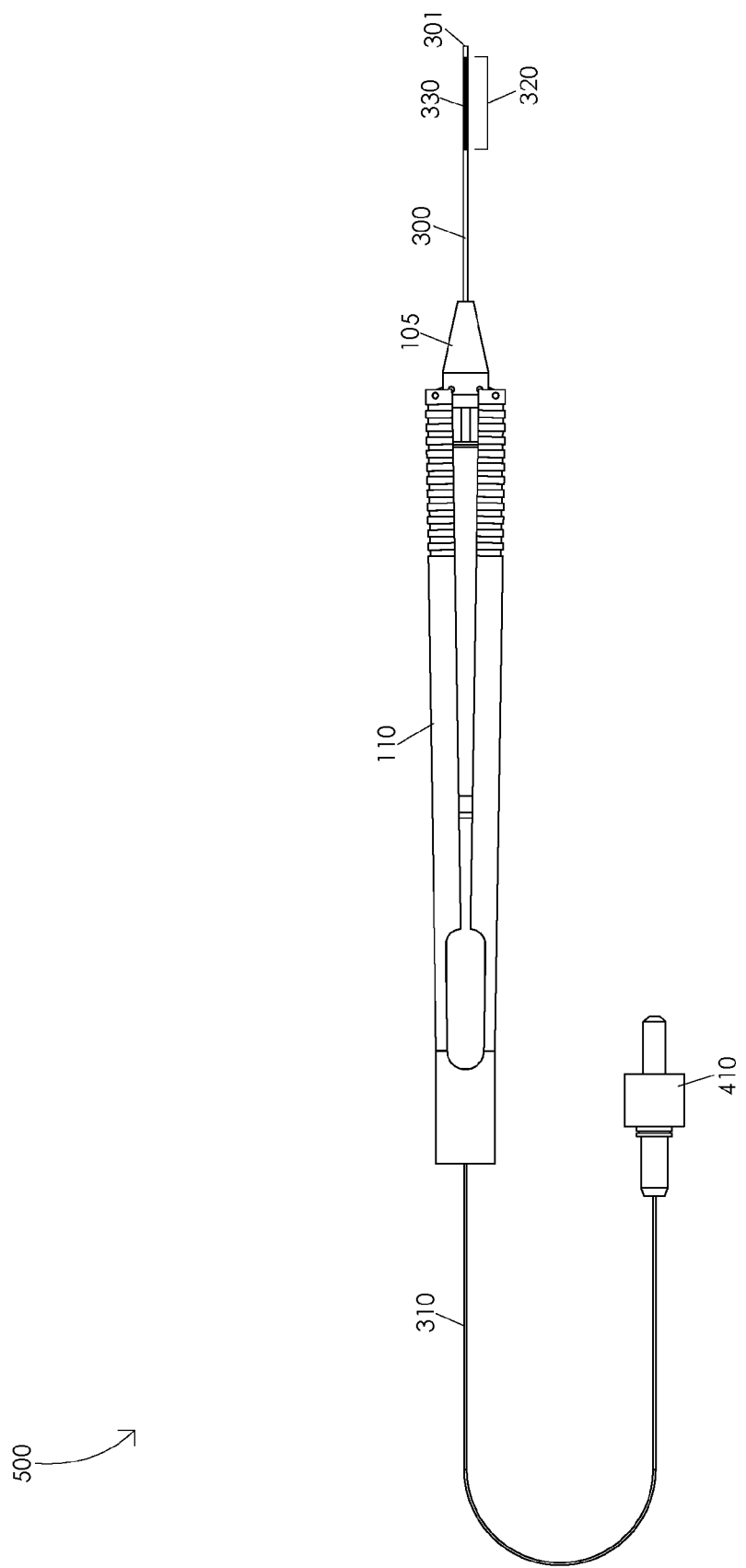
FIGS. 5A, 5B, 5C, 5D, and 5E are schematic diagrams illustrating a gradual curving of an optic fiber.

FIGS. 5A, 5B, 5C, 5D, and 5E are schematic diagrams illustrating a gradual curving of an optic fiber 310. FIG. 5A illustrates a straight optic fiber 500. In one or more embodiments, optic fiber 310 may comprise a straight optic fiber 500, e.g., when housing tube 300 is fully retracted relative to optic fiber 310. Illustratively, optic fiber 310 may comprise a straight optic fiber 500, e.g., when actuation structure 110 is fully decompressed. In one or more embodiments, optic fiber 310 may comprise a straight optic fiber 500, e.g., when nosecone 105 is fully retracted relative to handle proximal end 202. For example, optic fiber 310 may comprise a straight optic fiber 500, e.g., when first housing tube portion 320 is fully decompressed. Illustratively, a line tangent to optic fiber distal end 311 may be parallel to a line tangent to housing tube proximal end 302, e.g., when optic fiber 310 comprises a straight optic fiber 500.

Figure 5B:
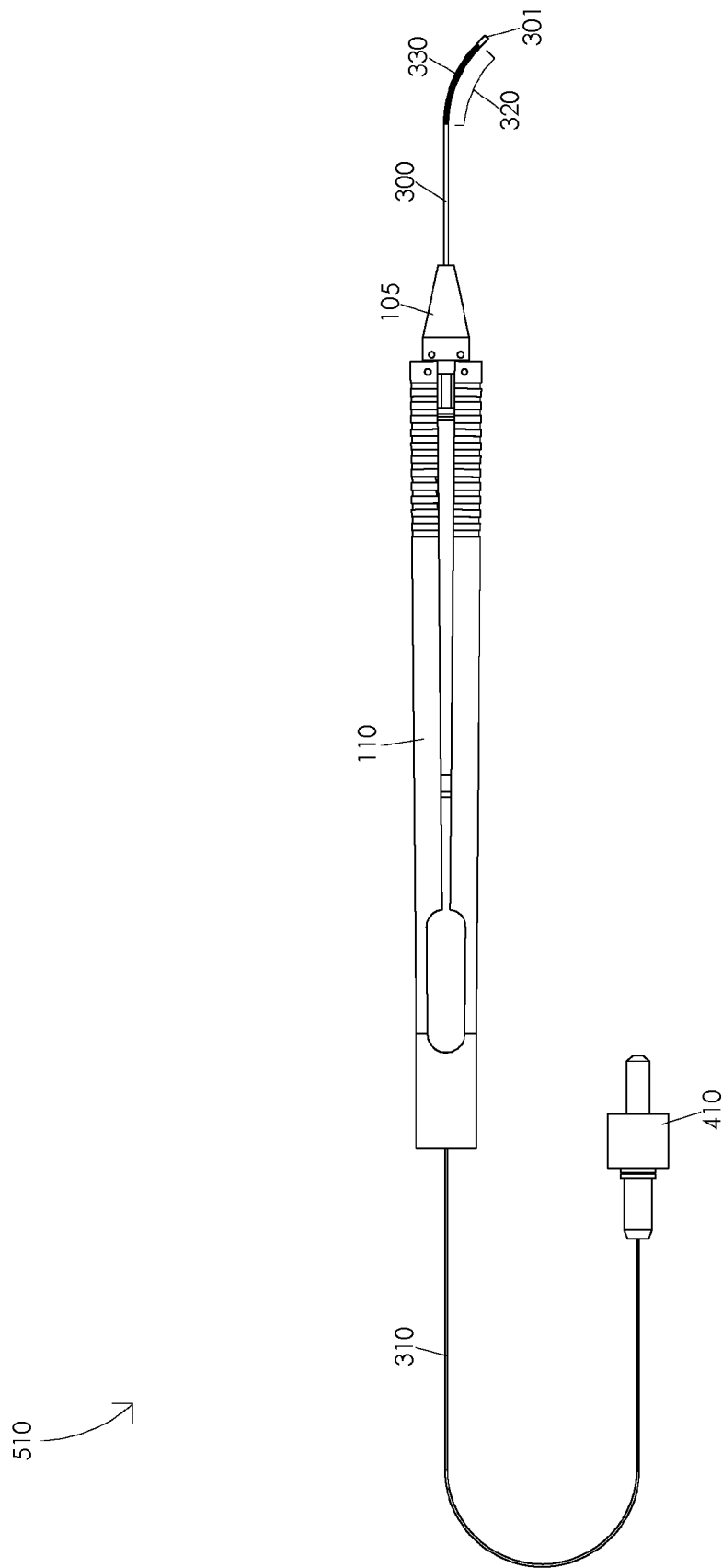

FIG. 5B illustrates an optic fiber in a first curved position 510. In one or more embodiments, a compression of actuation structure 110 may be configured to gradually curve optic fiber 310 from a straight optic fiber 500 to an optic fiber in a first curved position 510. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 202. Illustratively, an extension of nosecone 105 relative to handle proximal end 202 may be configured to extend housing tube 300 relative to optic fiber 310. In one or more embodiments, an extension of housing tube 300 relative to optic fiber 310 may be configured to apply a force to a portion of housing tube 300, e.g., a portion of optic fiber 310 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from a straight optic fiber 500 to an optic fiber in a first curved position 510. In one or more embodiments, a line tangent to optic fiber distal end 311 may intersect a line tangent to housing tube proximal end 302 at a first angle, e.g., when optic fiber 310 comprises an optic fiber in a first curved position 510. In one or more embodiments, the first angle may comprise any angle greater than zero degrees. For example, the first angle may comprise a 45 degree angle.

Figure 5C:
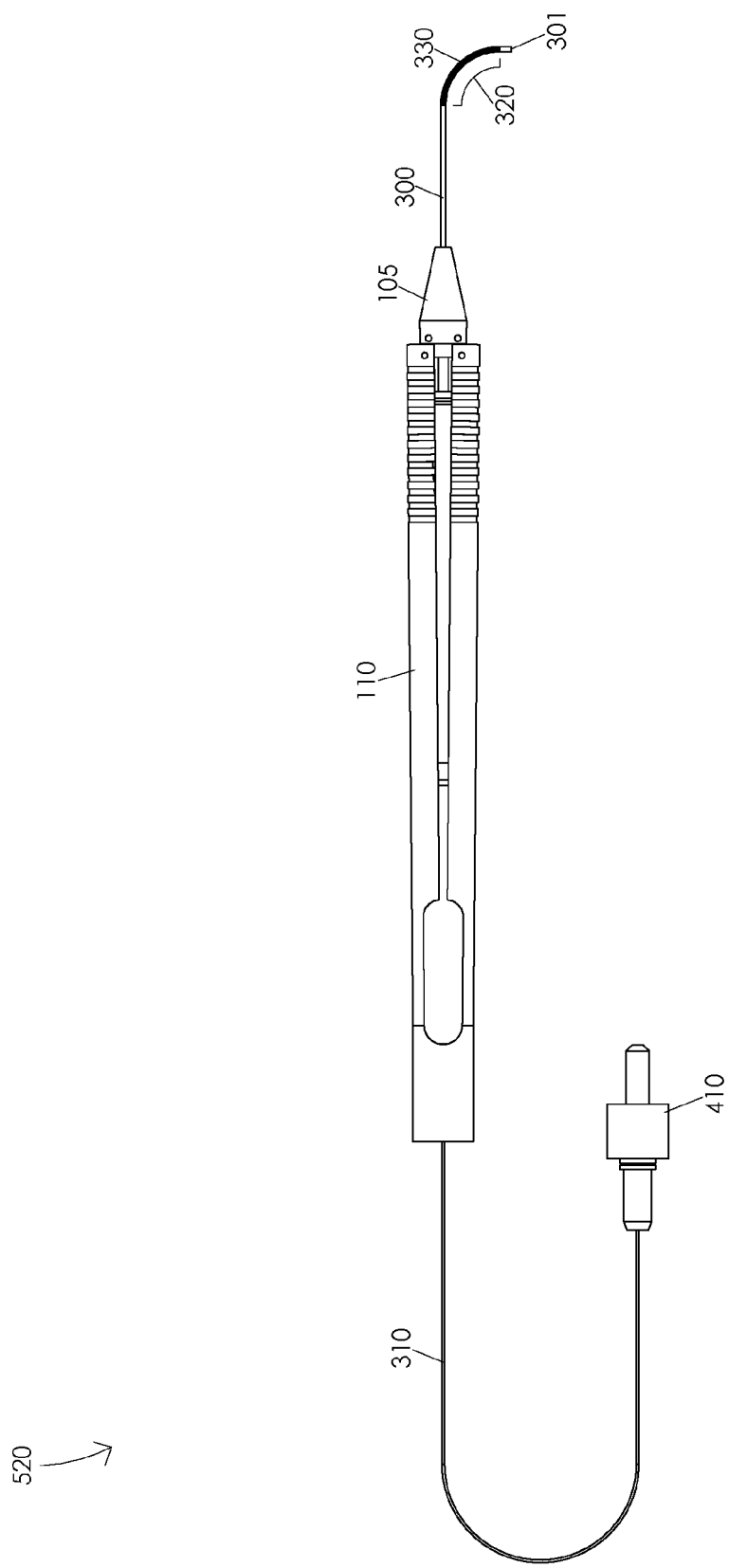

FIG. 5C illustrates an optic fiber in a second curved position 520. In one or more embodiments, a compression of actuation structure 110 may be configured to gradually curve optic fiber 310 from an optic fiber in a first curved position 510 to an optic fiber in a second curved position 520. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 202. Illustratively, an extension of nosecone 105 relative to handle proximal end 202 may be configured to extend housing tube 300 relative to optic fiber 310. In one or more embodiments, an extension of housing tube 300 relative to optic fiber 310 may be configured to apply a force to a portion of housing tube 300, e.g., a portion of optic fiber 310 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a first curved position 510 to an optic fiber in a second curved position 520. In one or more embodiments, a line tangent to optic fiber distal end 311 may intersect a line tangent to housing tube proximal end 302 at a second angle, e.g., when optic fiber 310 comprises an optic fiber in a second curved position 520. In one or more embodiments, the second angle may comprise any angle greater than the first angle. For example, the second angle may comprise a 90 degree angle.

Figure 5D:
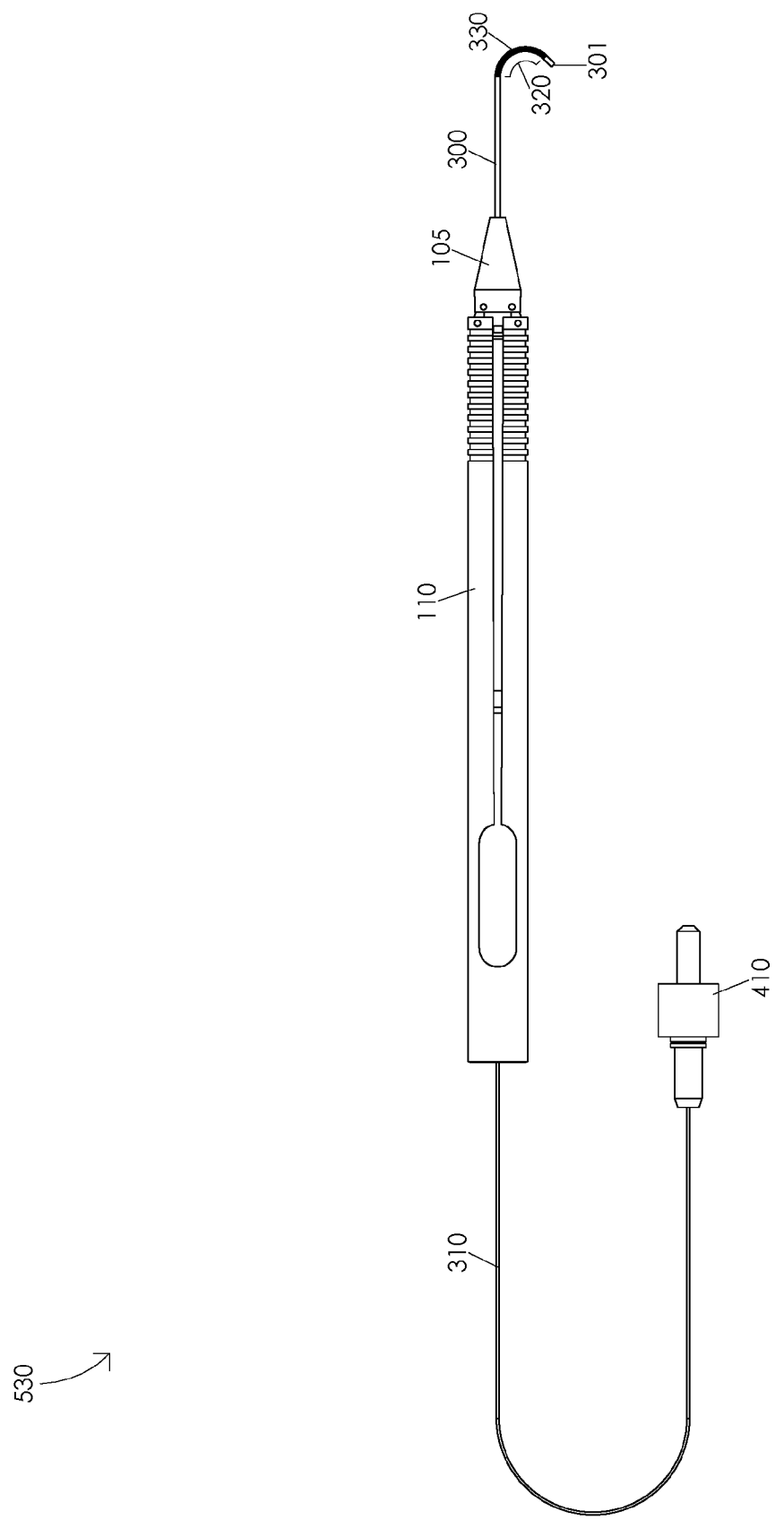

FIG. 5D illustrates an optic fiber in a third curved position 530. In one or more embodiments, a compression of actuation structure 110 may be configured to gradually curve optic fiber 310 from an optic fiber in a second curved position 520 to an optic fiber in a third curved position 530. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 202. Illustratively, an extension of nosecone 105 relative to handle proximal end 202 may be configured to extend housing tube 300 relative to optic fiber 310. In one or more embodiments, an extension of housing tube 300 relative to optic fiber 310 may be configured to apply a force to a portion of housing tube 300, e.g., a portion of optic fiber 310 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a second curved position 520 to an optic fiber in a third curved position 530. In one or more embodiments, a line tangent to optic fiber distal end 311 may intersect a line tangent to housing tube proximal end 302 at a third angle, e.g., when optic fiber 310 comprises an optic fiber in a third curved position 530. In one or more embodiments, the third angle may comprise any angle greater than the second angle. For example, the third angle may comprise a 135 degree angle.

Figure 5E:
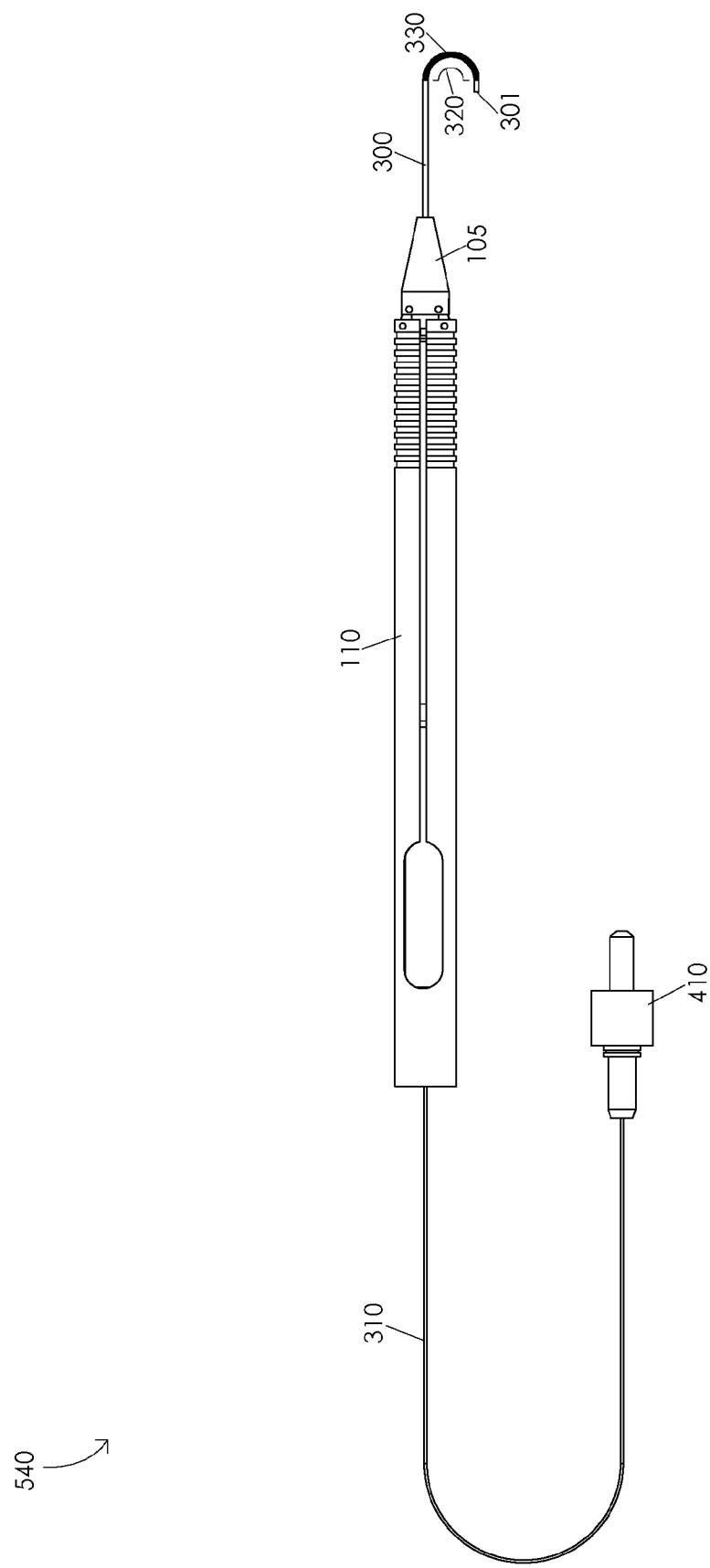

FIG. 5E illustrates an optic fiber in a fourth curved position 540. In one or more embodiments, a compression of actuation structure 110 may be configured to gradually curve optic fiber 310 from an optic fiber in a third curved position 530 to an optic fiber in a fourth curved position 540. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 202. Illustratively, an extension of nosecone 105 relative to handle proximal end 202 may be configured to extend housing tube 300 relative to optic fiber 310. In one or more embodiments, an extension of housing tube 300 relative to optic fiber 310 may be configured to apply a force to a portion of housing tube 300, e.g., a portion of optic fiber 310 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a third curved position 530 to an optic fiber in a fourth curved position 540. In one or more embodiments, a line tangent to optic fiber distal end 311 may be parallel to a line tangent to housing tube proximal end 302, e.g., when optic fiber 310 comprises an optic fiber in a fourth curved position 540.

In one or more embodiments, one or more properties of a steerable laser probe may be adjusted to attain one or more desired steerable laser probe features. Illustratively, a length that housing tube distal end 301 extends from nosecone distal end 106 may be adjusted to vary an amount of compression of actuation structure 110 configured to curve housing tube 300 to a particular curved position. In one or more embodiments, a stiffness of first housing tube portion 320 or a stiffness of second housing tube portion 330 may be adjusted to vary an amount of compression of actuation structure 110 configured to curve housing tube 300 to a particular curved position. Illustratively, a material comprising first housing tube portion 320 or a material comprising second housing tube portion 330 may be adjusted to vary an amount of compression of actuation structure 110 configured to curve housing tube 300 to a particular curved position.

In one or more embodiments, a number of apertures in housing tube 300 may be adjusted to vary an amount of compression of actuation structure 110 configured to curve housing tube 300 to a particular curved position. Illustratively, a location of one or more apertures in housing tube 300 may be adjusted to vary an amount of compression of actuation structure 110 configured to curve housing tube 300 to a particular curved position. In one or more embodiments, a geometry of one or more apertures in housing tube 300 may be adjusted to vary an amount of compression of actuation structure 110 configured to curve housing tube 300 to a particular curved position. Illustratively, a geometry of one or more apertures in housing tube 300 may be uniform, e.g., each aperture of the one or more apertures may have a same geometry. In one or more embodiments, a geometry of one or more apertures in housing tube 300 may be non-uniform, e.g., a first aperture in housing tube 300 may have a first geometry and a second aperture in housing tube 300 may have a second geometry. Illustratively, a geometry or location of one or more apertures in housing tube 300 may be optimized to evenly distribute an applied force. For example, a geometry or location of one or more apertures in housing tube 300 may be optimized to evenly distribute a force applied to first housing tube portion 320.

Illustratively, a stiffness of first housing tube portion 320 or a stiffness of second housing tube portion 330 may be adjusted to vary a bend radius of housing tube 300. In one or more embodiments, a stiffness of first housing tube portion 320 or a stiffness of second housing tube portion 330 may be adjusted to vary a radius of curvature of housing tube 300, e.g., when housing tube 300 is in a particular curved position. Illustratively, a number of apertures in housing tube 300 may be adjusted to vary a bend radius of housing tube 300. In one or more embodiments, a number of apertures in housing tube 300 may be adjusted to vary a radius of curvature of housing tube 300, e.g., when housing tube 300 is in a particular curved position. Illustratively, a location or a geometry of one or more apertures in housing tube 300 may be adjusted to vary a bend radius of housing tube 300. In one or more embodiments, a location or a geometry of one or more apertures in housing tube 300 may be adjusted to vary a radius of curvature of housing tube 300, e.g., when housing tube 300 is in a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, an optic fiber sleeve may be configured to compress a portion of housing tube 300, e.g., first housing tube portion 320. For example, an optic fiber sleeve may be disposed over a portion of optic fiber 310 fixed within optic fiber housing 210 and the optic fiber sleeve may be disposed over a portion of optic fiber 310 fixed to a portion of housing tube 300. In one or more embodiments, a compression of actuation structure 110 may be configured to extend housing tube 300 relative to the optic fiber sleeve. Illustratively, an extension of housing tube 300 relative to the optic fiber sleeve may cause the optic fiber sleeve to apply a force to a portion of housing tube 300, e.g., first housing tube portion 320. Illustratively, an application of a force to a portion of housing tube 300 may be configured to compress a portion of housing tube 300 causing housing tube 300 to gradually curve.

Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to a compression of actuation structure 110. In one or more embodiments, a portion of a steerable laser probe, e.g., handle 200, may be marked in a manner configured to indicate a direction that optic fiber 310 may curve. For example, a portion of housing tube 300 may comprise a mark configured to indicate a direction that optic fiber 310 may curve. Illustratively, housing tube 300 may comprise a slight curve, e.g., a curve less than 7.5 degrees, when actuation structure 110 is fully decompressed. In one or more embodiments, housing tube 300 may comprise a slight curve configured to indicate a direction that optic fiber 310 may curve, e.g., due to a compression of actuation structure 110.

Illustratively, a steerable laser probe may comprise an actuation structure 110, a nosecone 105 fixed to actuation structure 110 by one or more links 170 and one or more link pins 180, a housing tube 300, and an optic fiber 310. In one or more embodiments, a compression of actuation structure 110 may be configured to extend nosecone 105 relative to actuation structure proximal end 112. Illustratively, an extension of nosecone 105 relative to actuation structure proximal end 112 may be configured to extend housing tube 300 relative to optic fiber 310. In one or more embodiments, an extension of housing tube 300 relative to optic fiber 310 may be configured to apply a force to housing tube 300. Illustratively an application of a force to housing tube 300 may be configured to compress a portion of housing tube 300. In one or more embodiments, a compression of a portion of housing tube 300 may cause housing tube 300 to gradually curve. Illustratively, a gradual curving of housing tube 300 may be configured to gradually curve optic fiber 310.

Figure 6A:
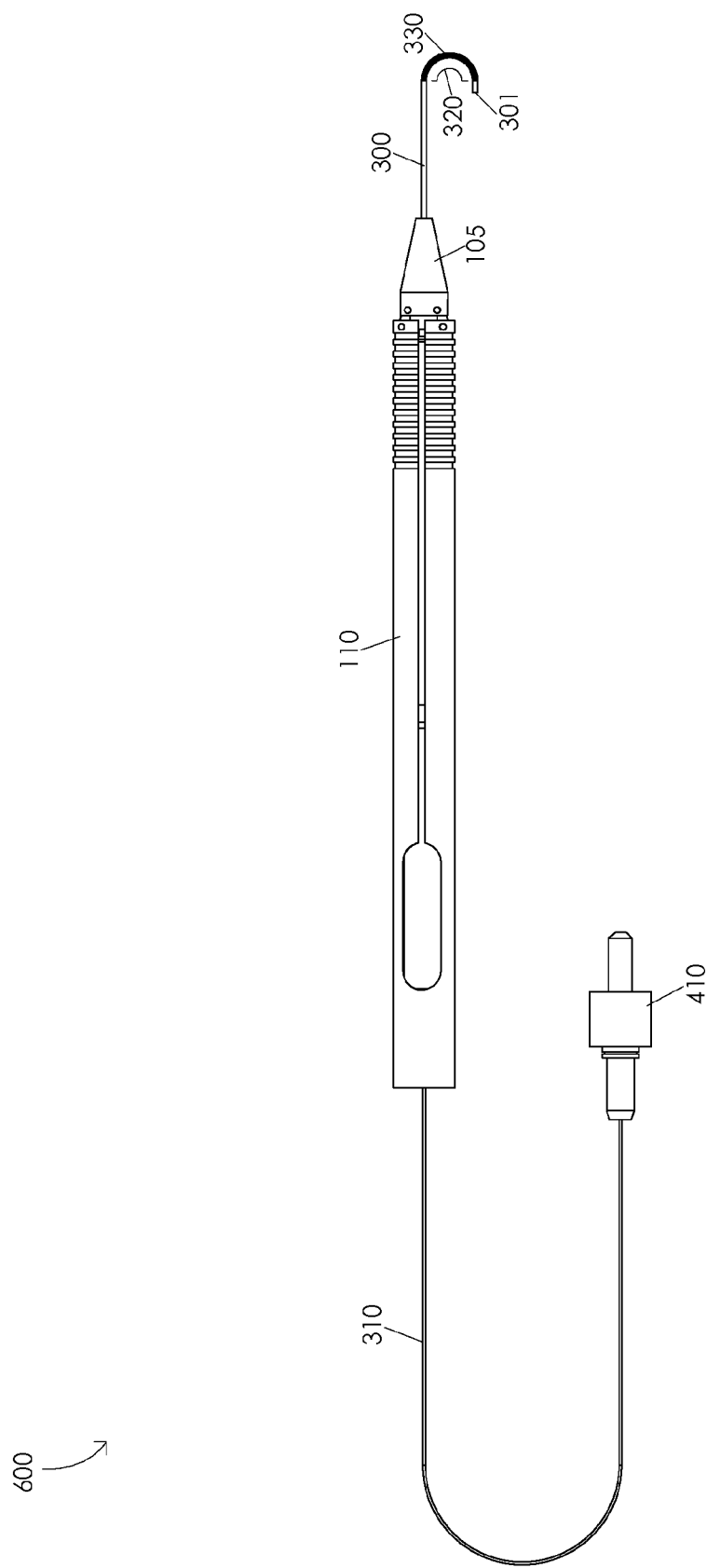
FIGS. 6A, 6B, 6C, 6D, and 6E are schematic diagrams illustrating a gradual straightening of an optic fiber.

FIGS. 6A, 6B, 6C, 6D, and 6E are schematic diagrams illustrating a gradual straightening of an optic fiber 310. FIG. 6A illustrates a fully curved optic fiber 600. In one or more embodiments, optic fiber 310 may comprise a fully curved optic fiber 600, e.g., when housing tube 300 is fully extended relative to optic fiber 310. Illustratively, optic fiber 310 may comprise a fully curved optic fiber 600, e.g., when actuation structure 110 is fully compressed. In one or more embodiments, optic fiber 310 may comprise a fully curved optic fiber 600, e.g., when nosecone 105 is fully extended relative to handle proximal end 202. For example, optic fiber 310 may comprise a fully curved optic fiber 600, e.g., when first housing tube portion 320 is fully compressed. Illustratively, a line tangent to optic fiber distal end 311 may be parallel to a line tangent to housing tube proximal end 302, e.g., when optic fiber 310 comprises a fully curved optic fiber 600.

Figure 6B:
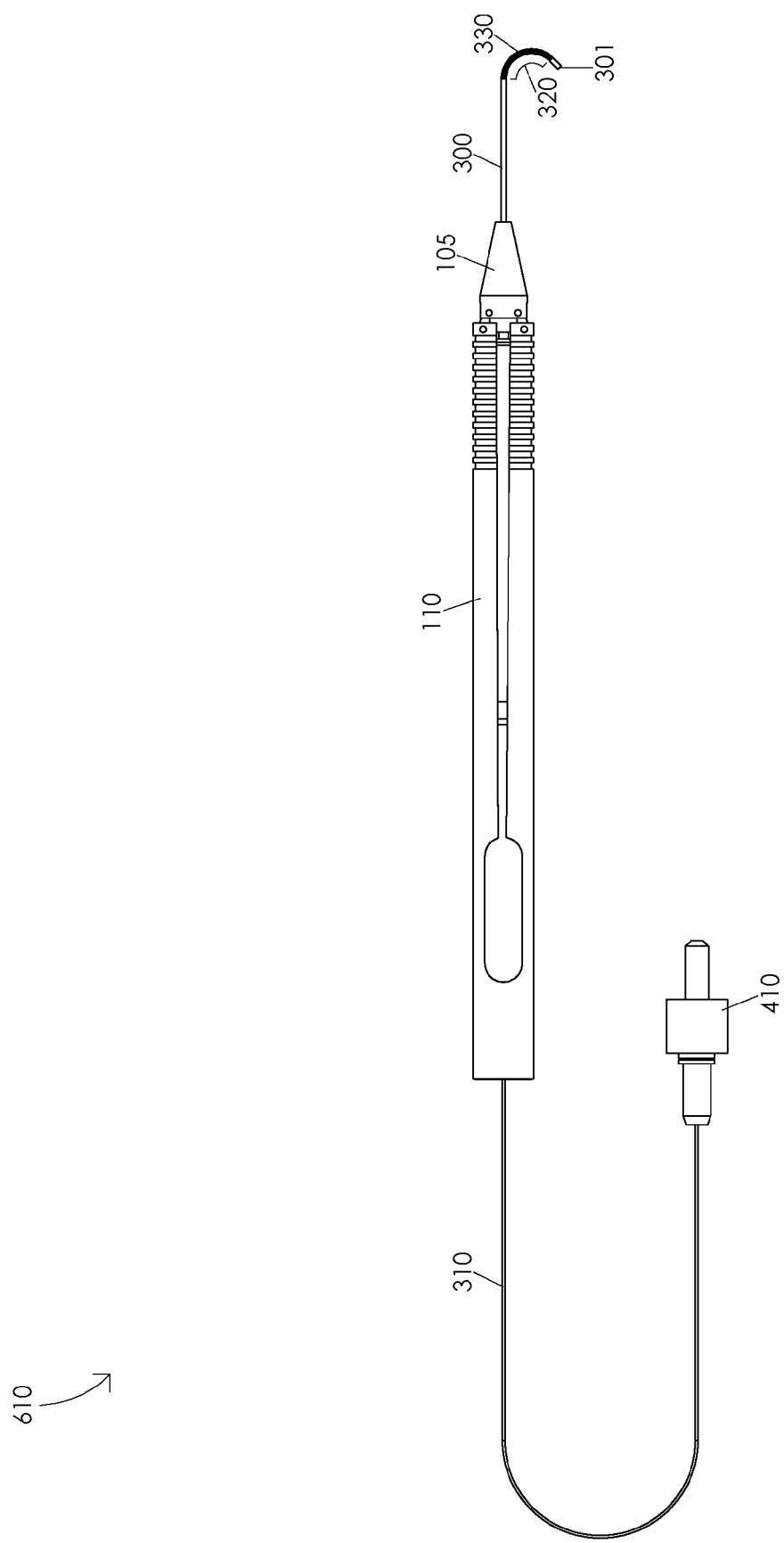

FIG. 6B illustrates an optic fiber in a first partially straightened position 610. In one or more embodiments, a decompression of actuation structure 110 may be configured to gradually straighten optic fiber 310 from a fully curved optic fiber 600 to an optic fiber in a first partially straightened position 610. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 202. Illustratively, a retraction of nosecone 105 relative to handle proximal end 202 may be configured to retract housing tube 300 relative to optic fiber 310. In one or more embodiments, a retraction of housing tube 300 relative to optic fiber 310 may be configured to reduce a force applied to a portion of housing tube 300, e.g., a portion of optic fiber 310 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from a fully curved optic fiber 600 to an optic fiber in a first partially straightened position 610. In one or more embodiments, a line tangent to optic fiber distal end 311 may intersect a line tangent to housing tube proximal end 302 at a first partially straightened angle, e.g., when optic fiber 310 comprises an optic fiber in a first partially straightened position 610. Illustratively, the first partially straightened angle may comprise any angle less than 180 degrees. For example, the first partially straightened angle may comprise a 135 degree angle.

Figure 6C:
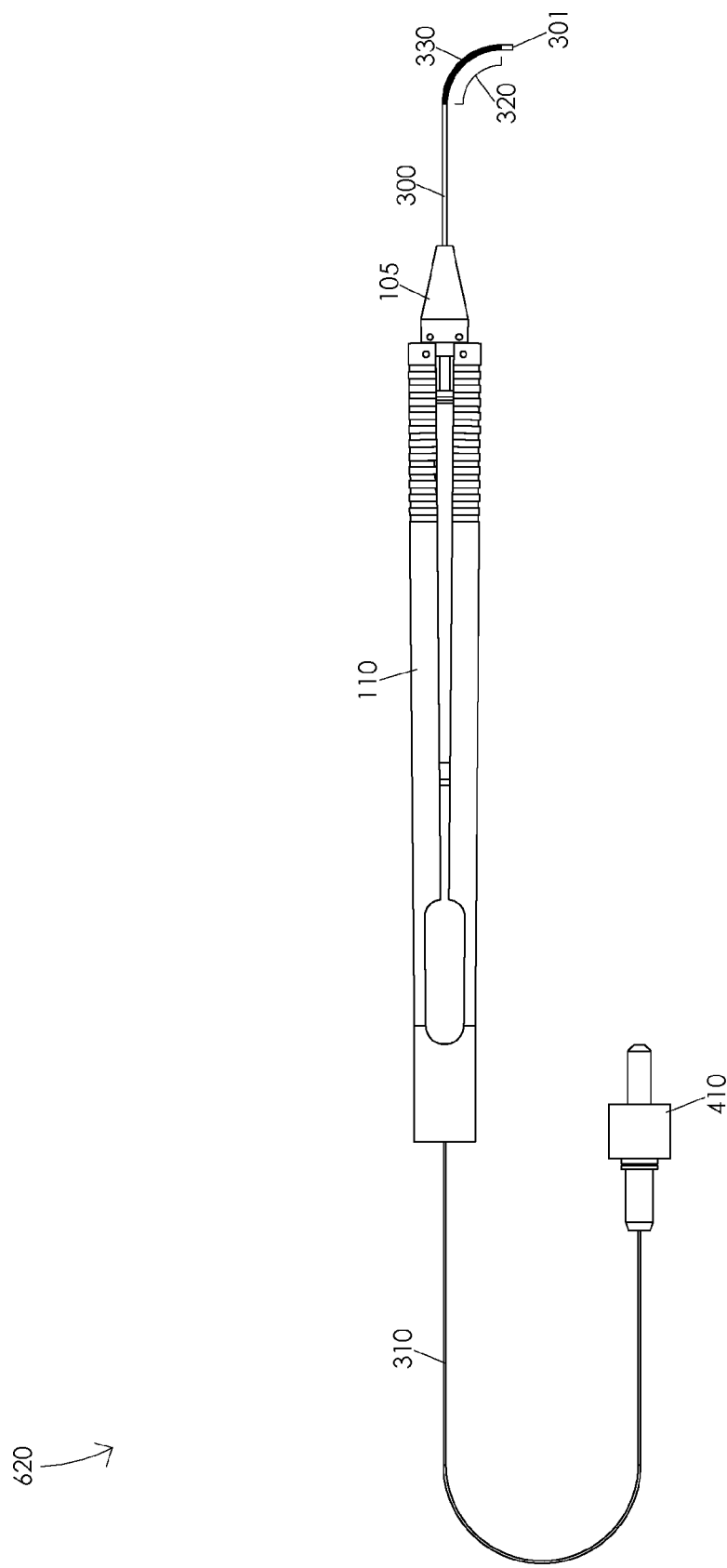

FIG. 6C illustrates an optic fiber in a second partially straightened position 620. In one or more embodiments, a decompression of actuation structure 110 may be configured to gradually straighten optic fiber 310 from an optic fiber in a first partially straightened position 610 to an optic fiber in a second partially straightened position 620. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 202. Illustratively, a refraction of nosecone 105 relative to handle proximal end 202 may be configured to retract housing tube 300 relative to optic fiber 310. In one or more embodiments, a refraction of housing tube 300 relative to optic fiber 310 may be configured to reduce a force applied to a portion of housing tube 300, e.g., a portion of optic fiber 310 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a first partially straightened position 610 to an optic fiber in a second partially straightened position 620. In one or more embodiments, a line tangent to optic fiber distal end 311 may intersect a line tangent to housing tube proximal end 302 at a second partially straightened angle, e.g., when optic fiber 310 comprises an optic fiber in a second partially straightened position 620. Illustratively, the second partially straightened angle may comprise any angle less than the first partially straightened angle. For example, the second partially straightened angle may comprise a 90 degree angle.

Figure 6D:
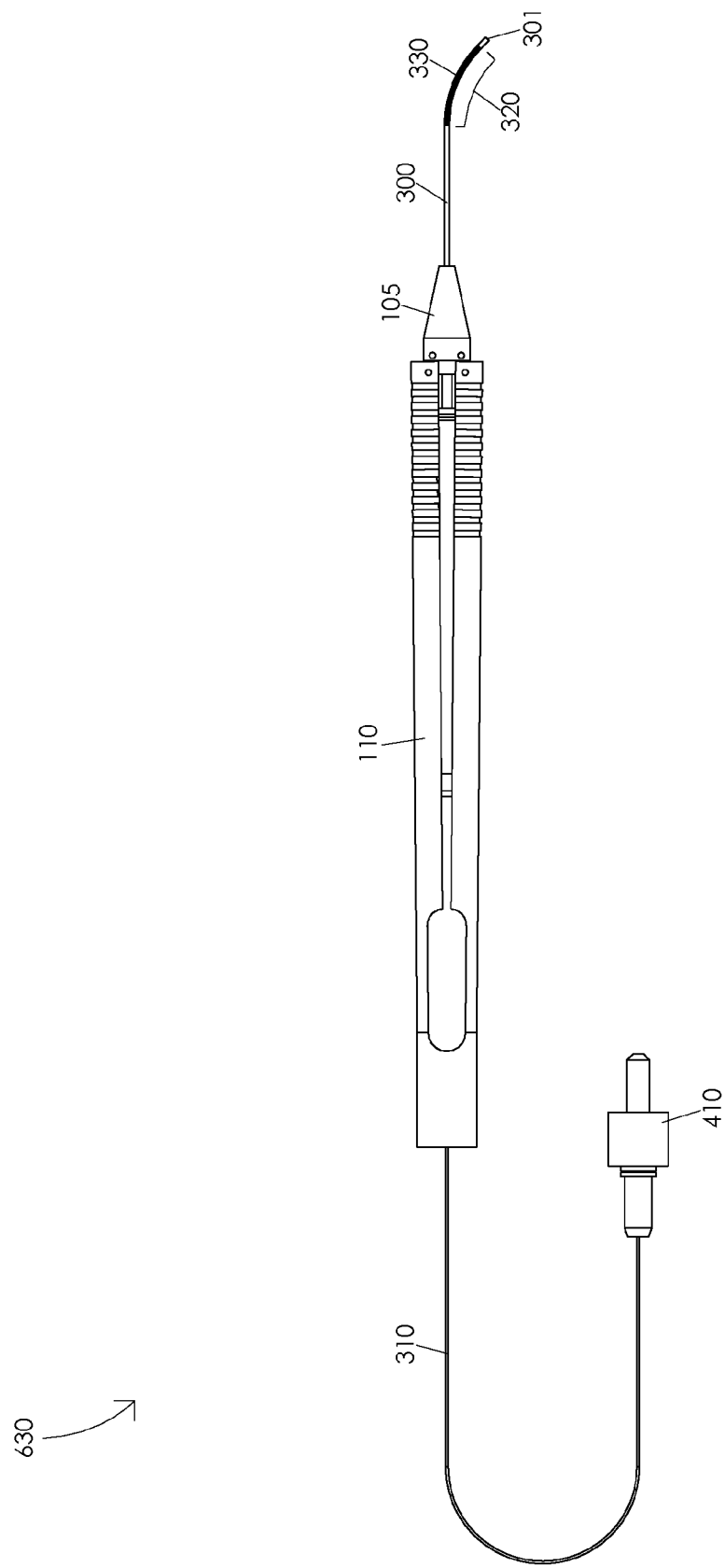

FIG. 6D illustrates an optic fiber in a third partially straightened position 630. In one or more embodiments, a decompression of actuation structure 110 may be configured to gradually straighten optic fiber 310 from an optic fiber in a second partially straightened position 620 to an optic fiber in a third partially straightened position 630. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 202. Illustratively, a refraction of nosecone 105 relative to handle proximal end 202 may be configured to retract housing tube 300 relative to optic fiber 310. In one or more embodiments, a refraction of housing tube 300 relative to optic fiber 310 may be configured to reduce a force applied to a portion of housing tube 300, e.g., a portion of optic fiber 310 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a second partially straightened position 620 to an optic fiber in a third partially straightened position 630. In one or more embodiments, a line tangent to optic fiber distal end 311 may intersect a line tangent to housing tube proximal end 302 at a third partially straightened angle, e.g., when optic fiber 310 comprises an optic fiber in a third partially straightened position 630. Illustratively, the third partially straightened angle may comprise any angle less than the second partially straightened angle. For example, the third partially straightened angle may comprise a 45 degree angle.

Figure 6E:
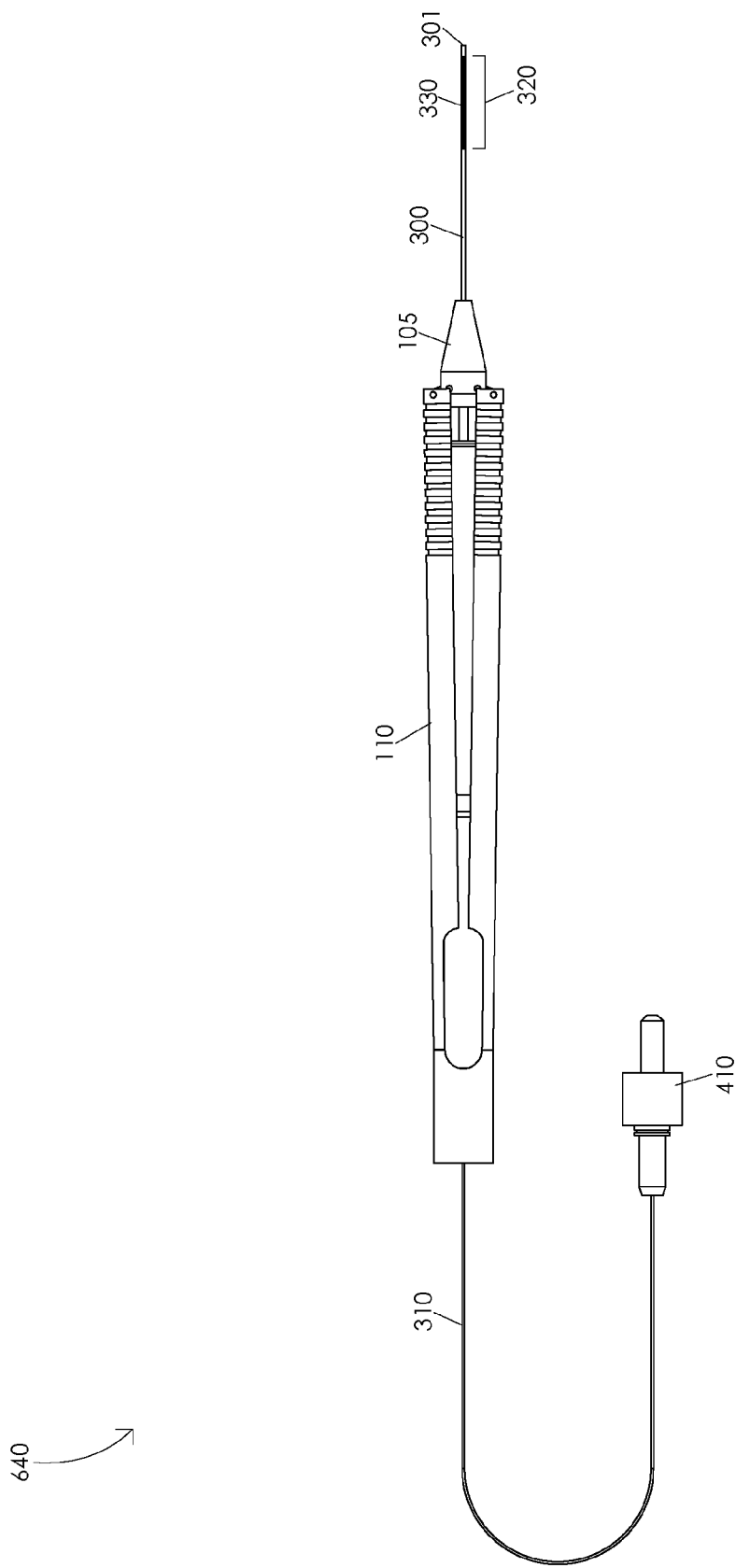

FIG. 6E illustrates an optic fiber in a fully straightened position 640. In one or more embodiments, a decompression of actuation structure 110 may be configured to gradually straighten optic fiber 310 from an optic fiber in a third partially straightened position 630 to an optic fiber in a fully straightened position 640. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 202. Illustratively, a retraction of nosecone 105 relative to handle proximal end 202 may be configured to retract housing tube 300 relative to optic fiber 310. In one or more embodiments, a retraction of housing tube 300 relative to optic fiber 310 may be configured to reduce a force applied to a portion of housing tube 300, e.g., a portion of optic fiber 310 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a third partially straightened position 630 to an optic fiber in a fully straightened position 640. In one or more embodiments, a line tangent to optic fiber distal end 311 may be parallel to a line tangent to housing tube proximal end 302, e.g., when optic fiber 310 comprises an optic fiber in a fully straightened position 640.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 200 to orient housing tube 300 in an orientation configured to cause a curvature of housing tube 300 within the particular transverse plane of the inner eye and varying an amount of compression of actuation structure 110. Illustratively, a surgeon may aim optic fiber distal end 311 at any target within a particular sagittal plane of the inner eye by, e.g., rotating handle 200 to orient housing tube 300 in an orientation configured to cause a curvature of housing tube 300 within the particular sagittal plane of the inner eye and varying an amount of compression of actuation structure 110. In one or more embodiments, a surgeon may aim optic fiber distal end 311 at any target within a particular frontal plane of the inner eye by, e.g., varying an amount of actuation of compression of actuation structure 110 to orient a line tangent to optic fiber distal end 311 wherein the line tangent to optic fiber distal end 311 is within the particular frontal plane of the inner eye and rotating handle 200. Illustratively, a surgeon may aim optic fiber distal end 311 at any target located outside of the particular transverse plane, the particular sagittal plane, and the particular frontal plane of the inner eye, e.g., by varying a rotational orientation of handle 200 and varying an amount of compression of actuation structure 110. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

FIGS. 7A and 7B are schematic diagrams illustrating a handle 700. FIG. 7A illustrates a side view of a handle 700. Illustratively, handle 700 may comprise a handle distal end 701 and a handle proximal end 702. In one or more embodiments, a portion of nosecone 105 may be fixed to a portion of actuation structure 110, e.g., nosecone proximal end 107 may be fixed to actuation structure distal end 111. Illustratively, nosecone 105 may be fixed to actuation structure 110, e.g., by one or more links 170. In one or more embodiments, one or more link pins 180 may be configured to fix nosecone 105 to one or more links 170, e.g., a particular link pin 180 may be disposed within nosecone 105 and a particular link 170. Illustratively, one or more link pins 180 may be configured to fix actuation structure 110 to one or more links 170, e.g., a particular link pin 180 may be disposed within actuation structure 110 and a particular link 170. In one or more embodiments, a first link pin 180 may be configured to fix nosecone 105 to a particular link 170 and a second link pin 180 may be configured to fix actuation structure 110 to the particular link 175. Illustratively, one or more spacers 175 may be configured to prevent undesirable movement of one or more links 170 relative to one or more link pins 180, e.g., a particular spacer 175 may be disposed over a portion of a particular link pin 180 extending from a particular link 170.

In one or more embodiments, a portion of inner hypodermic tube 140 may be disposed within piston 150, e.g., inner hypodermic tube proximal end 142 may be disposed within piston 150. Illustratively, a portion of inner hypodermic tube 140 may be fixed within piston 150, e.g., by an adhesive or any suitable fixation means. In one or more embodiments, inner hypodermic tube proximal end 142 may be fixed within piston 150, e.g., by an adhesive or any suitable fixation means. Illustratively, actuation guide 130 may be disposed within outer sleeve 120. In one or more embodiments, actuation guide 130 may be fixed within outer sleeve 120, e.g., by an adhesive or any suitable fixation means. Illustratively, piston 150 may be disposed within actuation guide 130. In one or more embodiments, piston 150 may be configured to actuate within actuation guide 130.

In one or more embodiments, distal ring 116 may be disposed over a portion of front plug 115. Illustratively, front plug 115 may be configured to interface with a portion of outer sleeve 120, e.g., front plug 115 may be configured to interface with outer sleeve distal end 121. In one or more embodiments, front plug 115 may be configured to interface with a portion of actuation guide 130, e.g., front plug 115 may be configured to interface with actuation guide distal end 131. Illustratively, front plug 115 may be disposed within outer sleeve 120. In one or more embodiments, a portion of front plug 115 may be disposed within actuation guide 130. Illustratively, distal ring 116 may be disposed within actuation guide 130, e.g., distal ring 116 may be configured to form a hermetic seal within actuation guide 130.

In one or more embodiments, proximal ring 117 may be disposed over a portion of end plug 160. Illustratively, end plug 160 may be configured to interface with a portion of outer sleeve 120, e.g., end plug 160 may be configured to interface with outer sleeve proximal end 122. In one or more embodiments, end plug 160 may be configured to interface with a portion of actuation guide 130, e.g., end plug 160 may be configured to interface with actuation guide proximal end 132. For example, a portion of end plug 160 may be disposed within actuation guide 130. Illustratively, proximal ring 117 may be disposed within actuation guide 130, e.g., proximal ring 117 may be configured to form a hermetic seal within actuation guide 130. In one or more embodiments, end plug 160 may be disposed within outer sleeve 120. Illustratively, inner hypodermic tube 140 may be disposed within piston 150, actuation guide 130, front plug 115, distal ring 116, and nosecone 105. In one or more embodiments, a portion of inner hypodermic tube 140 may be fixed within nosecone 105, e.g., inner hypodermic tube distal end 141 may be fixed within nosecone 105. Illustratively, a portion of inner hypodermic tube 140 may be fixed within nosecone 105, e.g., by an adhesive or any suitable fixation means.

In one or more embodiments, a compression of actuation structure 110 may be configured to rotate one or more links 170 about one or more link pins 180. Illustratively, a rotation of one or more links 170 about one or more link pins 180 may be configured to extend a particular link pin 180, e.g., a particular link pin 180 disposed in nosecone 105, relative to handle proximal end 702. In one or more embodiments, an extension of a particular link pin 180 disposed in nosecone 105 relative to handle proximal end 702 may be configured to extend nosecone 105 relative to handle proximal end 702. Illustratively, a compression of actuation structure 110 may be configured to extend nosecone 105 relative to handle proximal end 702. In one or more embodiments, an extension of nosecone 105 relative to handle proximal end 702 may be configured to extend inner hypodermic tube 140 relative to handle proximal end 702. Illustratively, an extension of inner hypodermic tube 140 relative to handle proximal end 702 may be configured to actuate piston 150 within actuation guide 130. In one or more embodiments, a compression of actuation structure 110 may be configured to extend piston 150 relative to handle proximal end 702.

In one or more embodiments, a decompression of action structure 110 may be configured to rotate one or more links 170 about one or more link pins 180. Illustratively, a rotation of one or more links 170 about one or more link pins 180 may be configured to retract a particular link pin 180, e.g., a particular link pin 180 disposed in nosecone 105, relative to handle proximal end 702. In one or more embodiments, a retraction of a particular link pin 180 disposed in nosecone 105 relative to handle proximal end 702 may be configured to retract nosecone 105 relative to handle proximal end 702. Illustratively, a decompression of actuation structure 110 may be configured to retract nosecone 105 relative to handle proximal end 702. In one or more embodiments, a retraction of nosecone 105 relative to handle proximal end 702 may be configured to retract inner hypodermic tube 140 relative to handle proximal end 702. Illustratively, a retraction of inner hypodermic tube 140 relative to handle proximal end 702 may be configured to actuate piston 150 within actuation guide 130. In one or more embodiments, a decompression of actuation structure 110 may be configured to retract piston 150 relative to handle proximal end 702.

FIG. 7B illustrates a cross-sectional view of a handle 700. In one or more embodiments, handle 700 may comprise a cable housing 710, an inner bore 220, an optic fiber guide 230, and a housing tube housing 240. Illustratively, handle 700 may be manufactured from any suitable material, e.g., polymers, metals, metal alloys, etc., or from any combination of suitable materials.

Figure 8:
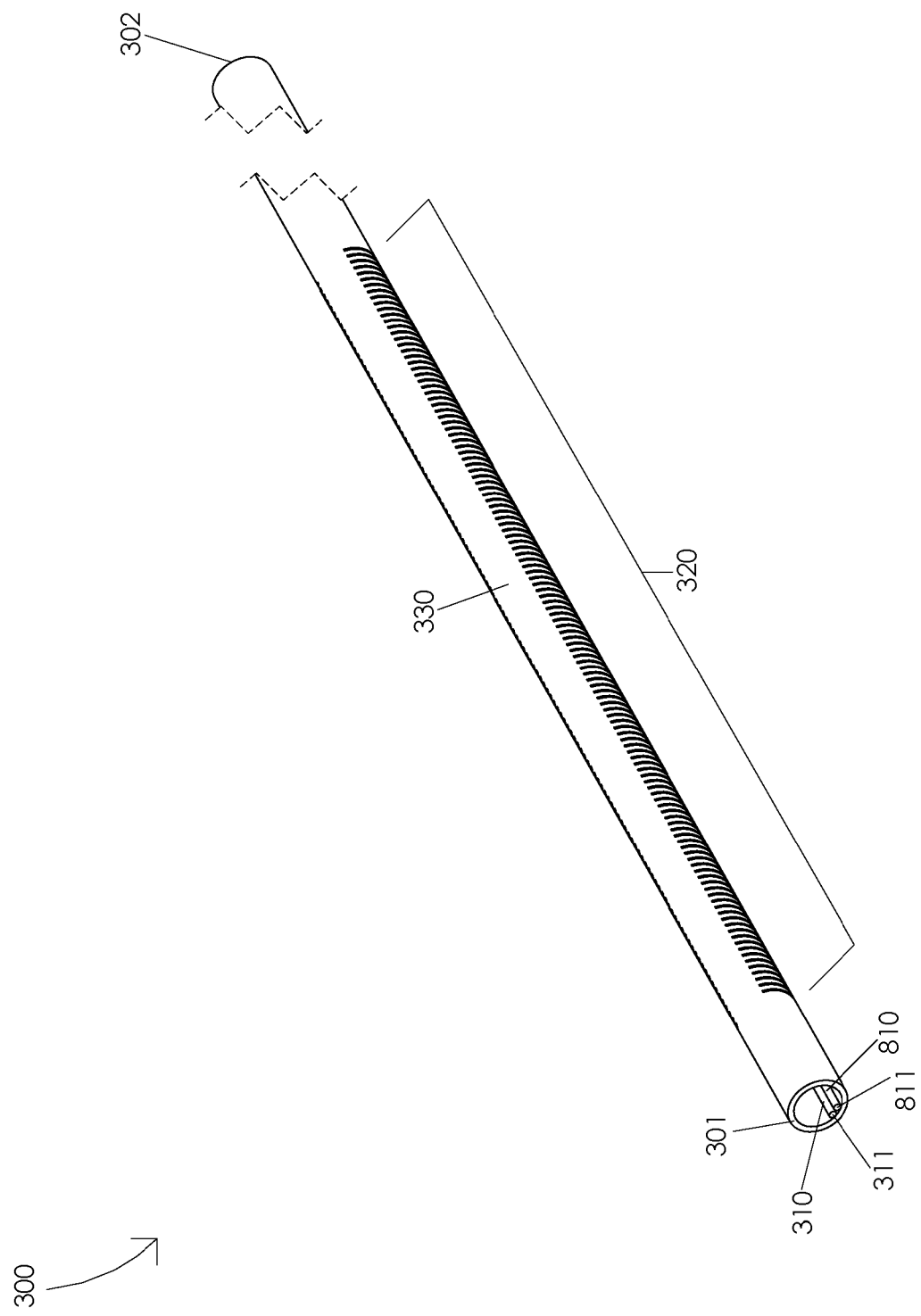
FIG. 8 is a schematic diagram illustrating a housing tube.

FIG. 8 is a schematic diagram illustrating a housing tube 300. Illustratively, an optic fiber 310 may be disposed within housing tube 300. In one or more embodiments, optic fiber 310 may comprise an optic fiber distal end 311 and an optic fiber proximal end 312. Illustratively, optic fiber 300 may be configured to transmit light, e.g., laser light, illumination light, etc. In one or more embodiments, optic fiber 310 may be disposed within housing tube 300 wherein optic fiber distal end 311 may be adjacent to housing tube distal end 301. Illustratively, optic fiber 310 may be disposed within housing tube 300 wherein a portion of optic fiber 310 may be adjacent to a portion of first housing tube portion 320. In one or more embodiments, a portion of optic fiber 310 may be fixed to an inner portion of housing tube 300, e.g., by an adhesive or any suitable fixation means.

Illustratively, a cable 810 may be disposed within housing tube 300. In one or more embodiments, cable 810 may comprise a cable distal end 811 and a cable proximal end 812. Illustratively, cable 810 may be disposed within housing tube 300 wherein cable distal end 811 may be adjacent to housing tube distal end 301. Illustratively, cable 810 may be disposed within housing tube 300 wherein a portion of cable 810 may be adjacent to a portion of first housing tube portion 320. In one or more embodiments, a portion of cable 810 may be fixed to a portion of housing tube 300, e.g., by an adhesive or any suitable fixation means. For example, cable 810 may be fixed to a portion of housing tube 300 by a weld, a mechanical means, a tie, etc.

Figure 9:
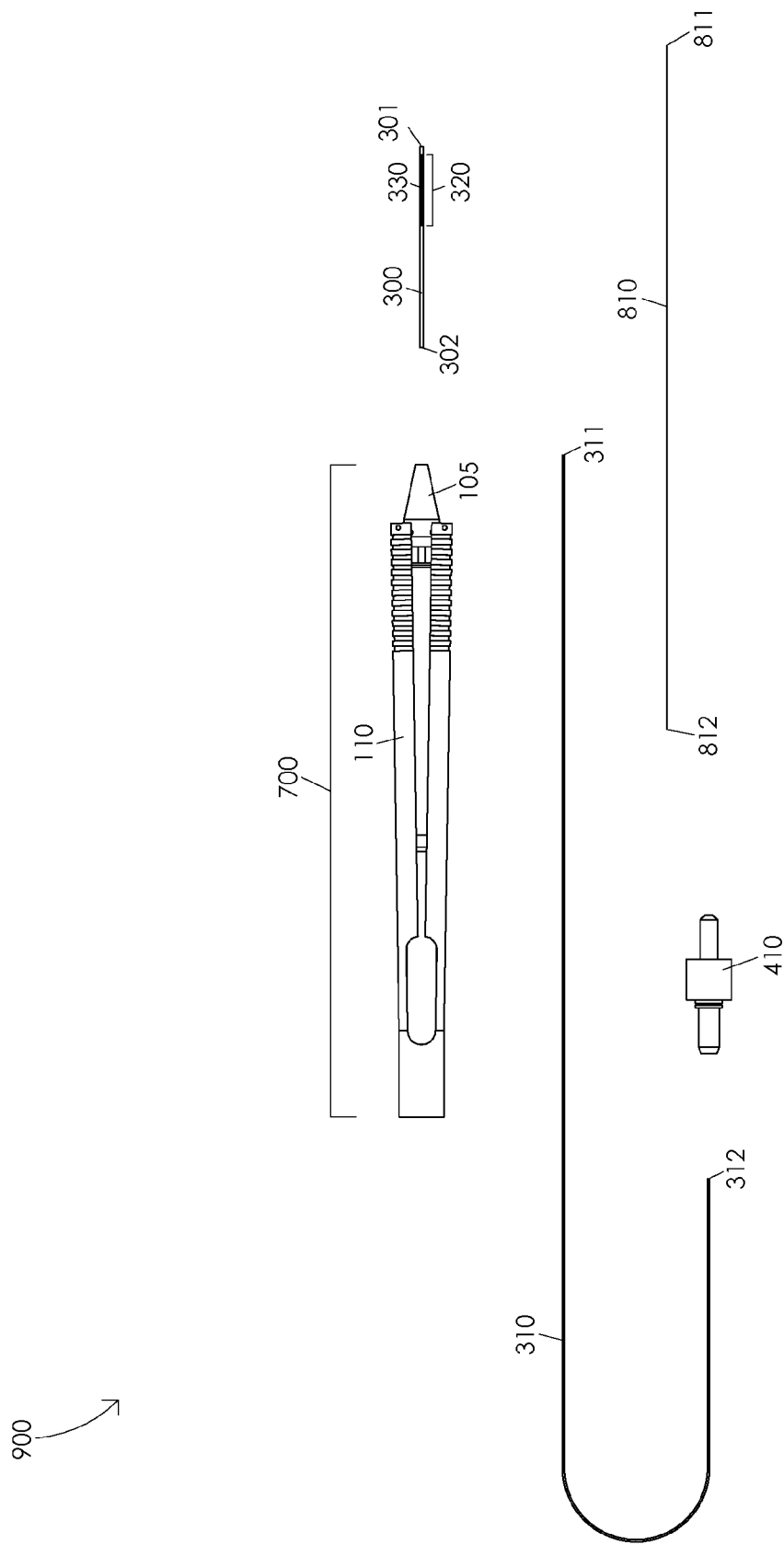
FIG. 9 is a schematic diagram illustrating an exploded view of a steerable laser probe assembly.

FIG. 9 is a schematic diagram illustrating an exploded view of a steerable laser probe assembly 900. Illustratively, a steerable laser probe assembly 900 may comprise a handle 700, a housing tube 300 having a housing tube distal end 301 and a housing tube proximal end 302, an optic fiber 310 having an optic fiber distal end 311 and an optic fiber proximal end 312, a cable 810 having a cable distal end 811 and a cable proximal end 812, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of housing tube 300 may be fixed to nosecone 105, e.g., housing tube proximal end 302 may be fixed to nosecone distal end 106. In one or more embodiments, a portion of housing tube 300 may be fixed to nosecone 105, e.g., by an adhesive or any suitable fixation means. Illustratively, a portion of housing tube 300 may be disposed within nosecone 105, e.g., housing tube proximal end 302 may be disposed within nosecone 105. In one or more embodiments, a portion of housing tube 300 may be fixed within nosecone 105, e.g., by an adhesive or any suitable fixation means. Illustratively, a portion of housing tube 300 may be disposed within housing tube housing 240, e.g., housing tube proximal end 302 may be disposed within housing tube housing 240. In one or more embodiments, a portion of housing tube 300 may be fixed within housing tube housing 240, e.g., by an adhesive or any suitable fixation means. For example, a portion of housing tube 300 may be fixed within housing tube housing 240 by a press fit, a weld, etc.

Illustratively, optic fiber 310 may be disposed within inner bore 220, optic fiber guide 230, piston 150, inner hypodermic tube 140, nosecone 105, and housing tube 300. In one or more embodiments, optic fiber 310 may be disposed within housing tube 300 wherein optic fiber distal end 311 is adjacent to housing tube distal end 301. Illustratively, optic fiber 310 may be disposed within housing tube 300 wherein a portion of optic fiber 310 is adjacent to first housing tube portion 320. In one or more embodiments, a portion of optic fiber 310 may be fixed to a portion of housing tube 300, e.g., by an adhesive or any suitable fixation means.

Illustratively, cable 810 may be disposed within cable housing 710, optic fiber guide 230, piston 150, inner hypodermic tube 140, nosecone 105, and housing tube 300. In one or more embodiment, cable 810 may be disposed within housing tube 300 wherein cable distal end 811 may be adjacent to housing tube distal end 301. Illustratively, cable 810 may be disposed within housing tube 300 wherein a portion of cable 810 may be adjacent to a portion of first housing tube portion 320. In one or more embodiments, a portion of cable 810 may be fixed to a portion of housing tube 300, e.g., by an adhesive or any suitable fixation means. For example, cable 810 may be fixed to a portion of housing tube 300 by a weld, a mechanical means, a tie, etc. Illustratively, a portion of cable 810 may be fixed in cable housing 710, e.g., cable proximal end 812 may be fixed in cable housing 710. In one or more embodiments, a portion of cable 810 may be fixed in cable housing 710, e.g., by an adhesive or any suitable fixation means. For example, a portion of cable 810 may be fixed in cable housing 710 by a press fit, a weld, a tie, etc. Illustratively, cable 810 may be fixed in cable housing 710 and cable 810 may be fixed to a portion of housing tube 300. Cable 810 may be manufactured from any suitable material, e.g., polymers, metals, metal alloys, etc., or from any combination of suitable materials.

In one or more embodiments, a compression of actuation structure 110 may be configured to rotate one or more links 170 about one or more link pins 180. Illustratively, a rotation of one or more links 170 about one or more link pins 180 may be configured to extend nosecone 105 relative to handle proximal end 702. In one or more embodiments, an extension of nosecone 105 relative to handle proximal end 702 may be configured to extend housing tube 300 relative to handle proximal end 702. Illustratively, an extension of housing tube 300 relative to handle proximal end 702 may be configured to extend housing tube 300 relative to cable 810. In one or more embodiments, a portion of cable 810, e.g., a portion of cable 810 fixed to housing tube 300, may be configured to resist an extension of housing tube 300 relative to cable 810. Illustratively, cable 810 may be fixed within cable housing 710 and cable 810 may be fixed to housing tube 300. In one or more embodiments, an extension of housing tube 300 relative to cable 810 may be configured to apply a force to a portion of housing tube 300. Illustratively, an application of a force to a portion of housing tube 300 may be configured to compress a portion of housing tube 300, e.g., an application of a force to a portion of housing tube 300 may be configured to compress first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310. In one or more embodiments, a compression of actuation structure 110 may be configured to gradually curve optic fiber 310. Illustratively, a compression of actuation structure 110 may be configured to gradually curve housing tube 300.

In one or more embodiments, a decompression of actuation structure 110 may be configured to rotate one or more links 170 about one or more link pins 180. Illustratively, a rotation of one or more links 170 about one or more link pins 180 may be configured to retract nosecone 105 relative to handle proximal end 702. In one or more embodiments, a refraction of nosecone 105 relative to handle proximal end 702 may be configured to retract housing tube 300 relative to handle proximal end 702. Illustratively, a retraction of housing tube 300 relative to handle proximal end 702 may be configured to retract housing tube 300 relative to cable 810. In one or more embodiments, a portion of cable 810, e.g., a portion of cable 810 fixed to housing tube 300, may be configured to facilitate a retraction of housing tube 300 relative to cable 810. Illustratively, cable 810 may be fixed within cable housing 710 and cable 810 may be fixed to housing tube 300. In one or more embodiments, a retraction of housing tube 300 relative to cable 810 may be configured to reduce a force applied to a portion of housing tube 300. Illustratively, a reduction of a force applied to a portion of housing tube 300 may be configured to decompress a portion of housing tube 300, e.g., a reduction of a force applied to a portion of housing tube 300 may be configured to decompress first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310. In one or more embodiments, a decompression of actuation structure 110 may be configured to gradually straighten optic fiber 310. Illustratively, a decompression of actuation structure 110 may be configured to gradually straighten housing tube 300.

Figure 10A:
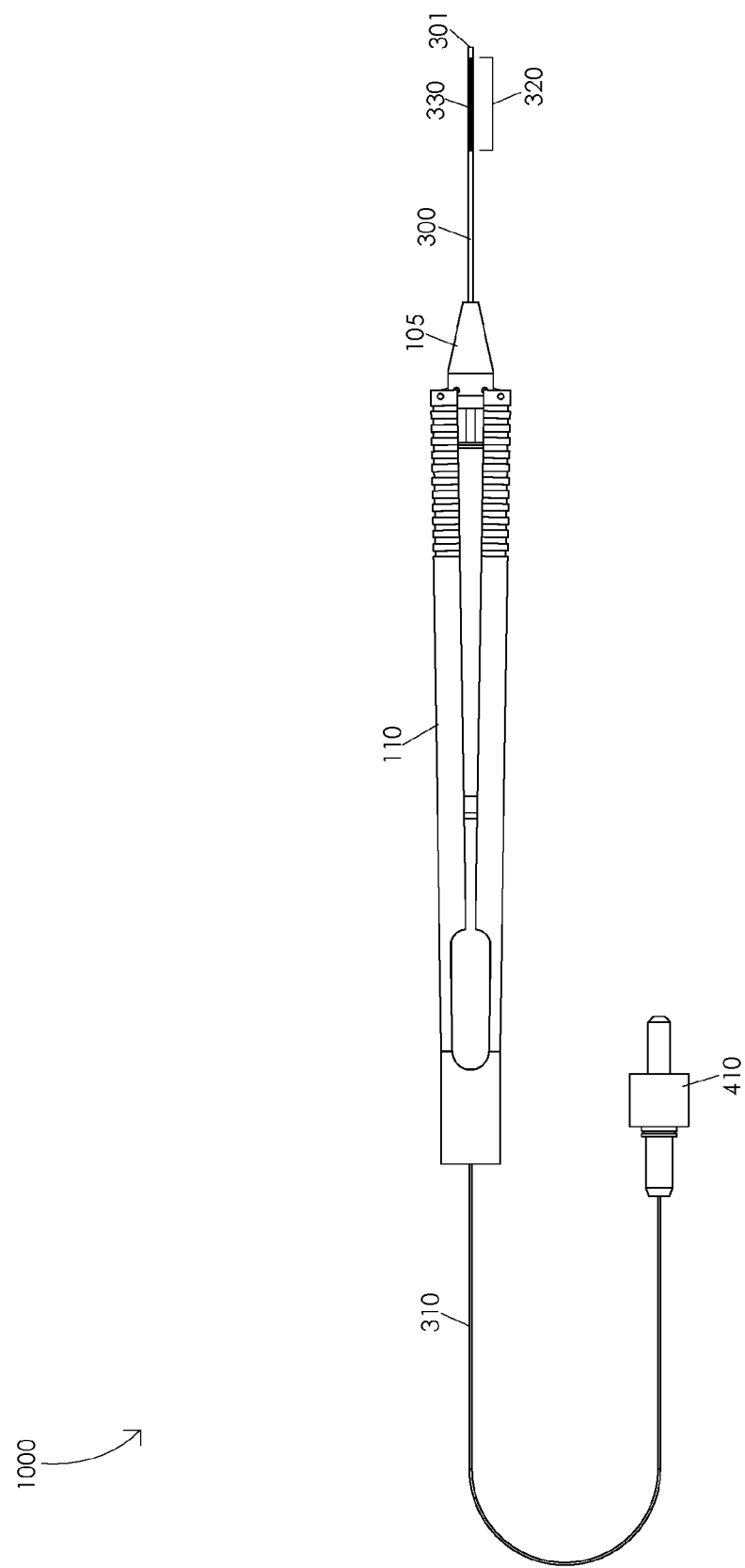
FIGS. 10A, 10B, 10C, 10D, and 10E are schematic diagrams illustrating a gradual curving of an optic fiber.

FIGS. 10A, 10B, 10C, 10D, and 10E are schematic diagrams illustrating a gradual curving of an optic fiber 310. FIG. 10A illustrates a straight optic fiber 1000. In one or more embodiments, optic fiber 310 may comprise a straight optic fiber 1000, e.g., when housing tube 300 is fully retracted relative to cable 810. Illustratively, optic fiber 310 may comprise a straight optic fiber 1000, e.g., when actuation structure 110 is fully decompressed. In one or more embodiments, optic fiber 310 may comprise a straight optic fiber 1000, e.g., when nosecone 105 is fully retracted relative to handle proximal end 702. For example, optic fiber 310 may comprise a straight optic fiber 1000, e.g., when first housing tube portion 320 is fully decompressed. Illustratively, a line tangent to optic fiber distal end 311 may be parallel to a line tangent to housing tube proximal end 302, e.g., when optic fiber 310 comprises a straight optic fiber 1000.

Figure 10B:
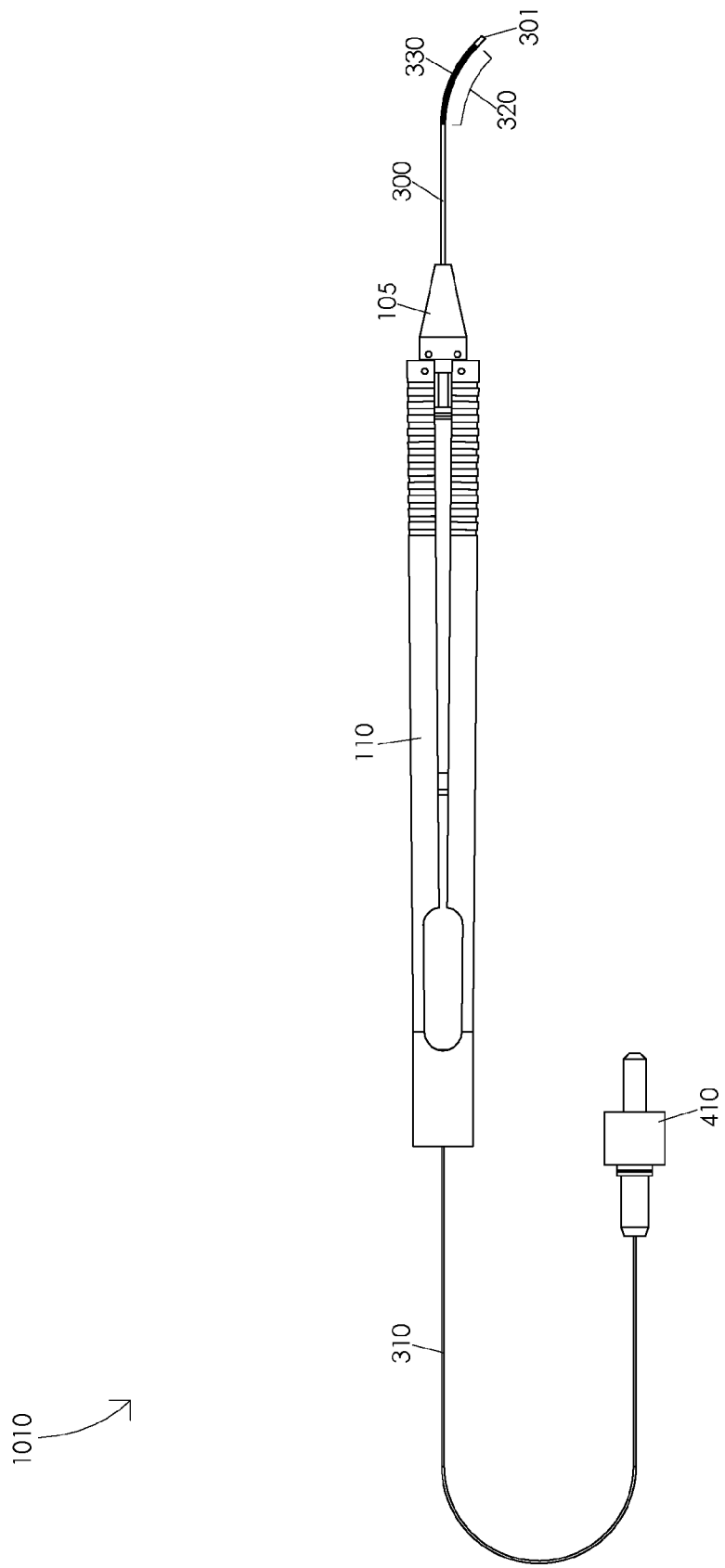

FIG. 10B illustrates an optic fiber in a first curved position 1010. In one or more embodiments, a compression of actuation structure 110 may be configured to gradually curve optic fiber 310 from a straight optic fiber 1000 to an optic fiber in a first curved position 1010. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 702. Illustratively, an extension of nosecone 105 relative to handle proximal end 702 may be configured to extend housing tube 300 relative to cable 810. In one or more embodiments, an extension of housing tube 300 relative to cable 810 may be configured to apply a force to a portion of housing tube 300, e.g., a portion of cable 810 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from a straight optic fiber 1000 to an optic fiber in a first curved position 1010. In one or more embodiments, a line tangent to optic fiber distal end 311 may intersect a line tangent to housing tube proximal end 302 at a first angle, e.g., when optic fiber 310 comprises an optic fiber in a first curved position 1010. In one or more embodiments, the first angle may comprise any angle greater than zero degrees. For example, the first angle may comprise a 45 degree angle.

Figure 10C:
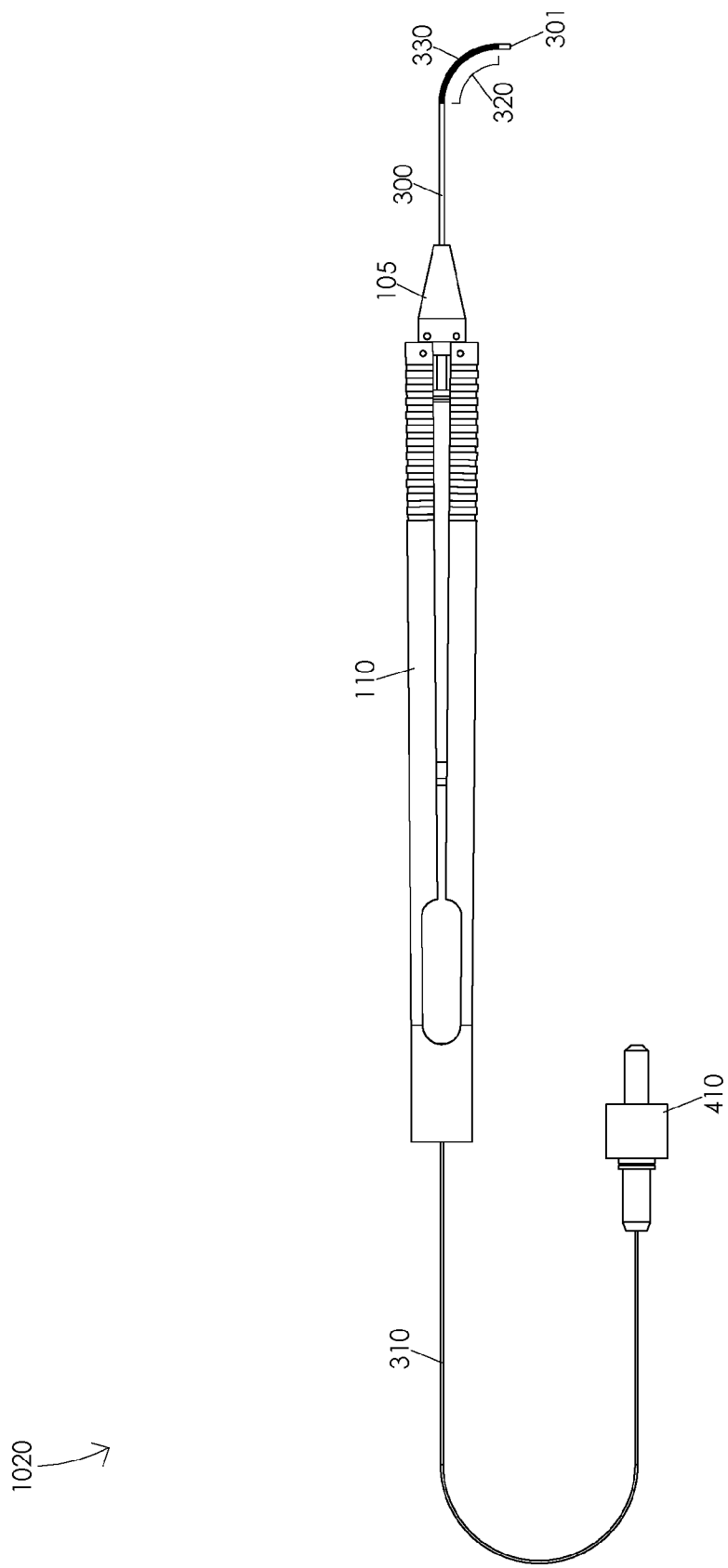

FIG. 10C illustrates an optic fiber in a second curved position 1020. In one or more embodiments, a compression of actuation structure 110 may be configured to gradually curve optic fiber 310 from an optic fiber in a first curved position 1010 to an optic fiber in a second curved position 1020. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 702. Illustratively, an extension of nosecone 105 relative to handle proximal end 702 may be configured to extend housing tube 300 relative to cable 810. In one or more embodiments, an extension of housing tube 300 relative to cable 810 may be configured to apply a force to a portion of housing tube 300, e.g., a portion of cable 810 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a first curved position 1010 to an optic fiber in a second curved position 1020. In one or more embodiments, a line tangent to optic fiber distal end 311 may intersect a line tangent to housing tube proximal end 302 at a second angle, e.g., when optic fiber 310 comprises an optic fiber in a second curved position 1020. In one or more embodiments, the second angle may comprise any angle greater than the first angle. For example, the second angle may comprise a 90 degree angle.

Figure 10D:
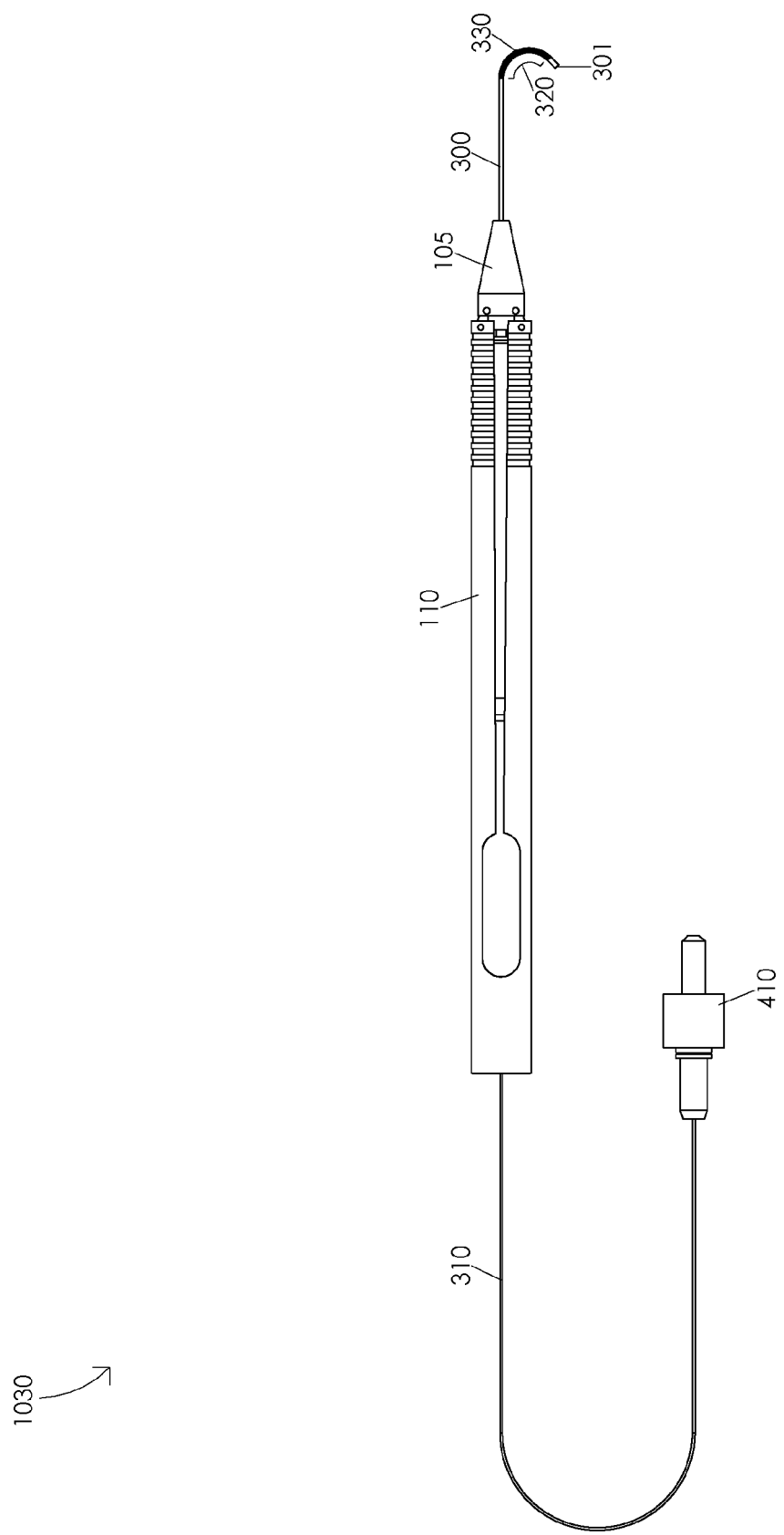

FIG. 10D illustrates an optic fiber in a third curved position 1030. In one or more embodiments, a compression of actuation structure 110 may be configured to gradually curve optic fiber 310 from an optic fiber in a second curved position 1020 to an optic fiber in a third curved position 1030. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 702. Illustratively, an extension of nosecone 105 relative to handle proximal end 702 may be configured to extend housing tube 300 relative to cable 810. In one or more embodiments, an extension of housing tube 300 relative to cable 810 may be configured to apply a force to a portion of housing tube 300, e.g., a portion of cable 810 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a second curved position 1020 to an optic fiber in a third curved position 1030. In one or more embodiments, a line tangent to optic fiber distal end 311 may intersect a line tangent to housing tube proximal end 302 at a third angle, e.g., when optic fiber 310 comprises an optic fiber in a third curved position 1030. In one or more embodiments, the third angle may comprise any angle greater than the second angle. For example, the third angle may comprise a 135 degree angle.

Figure 10E:
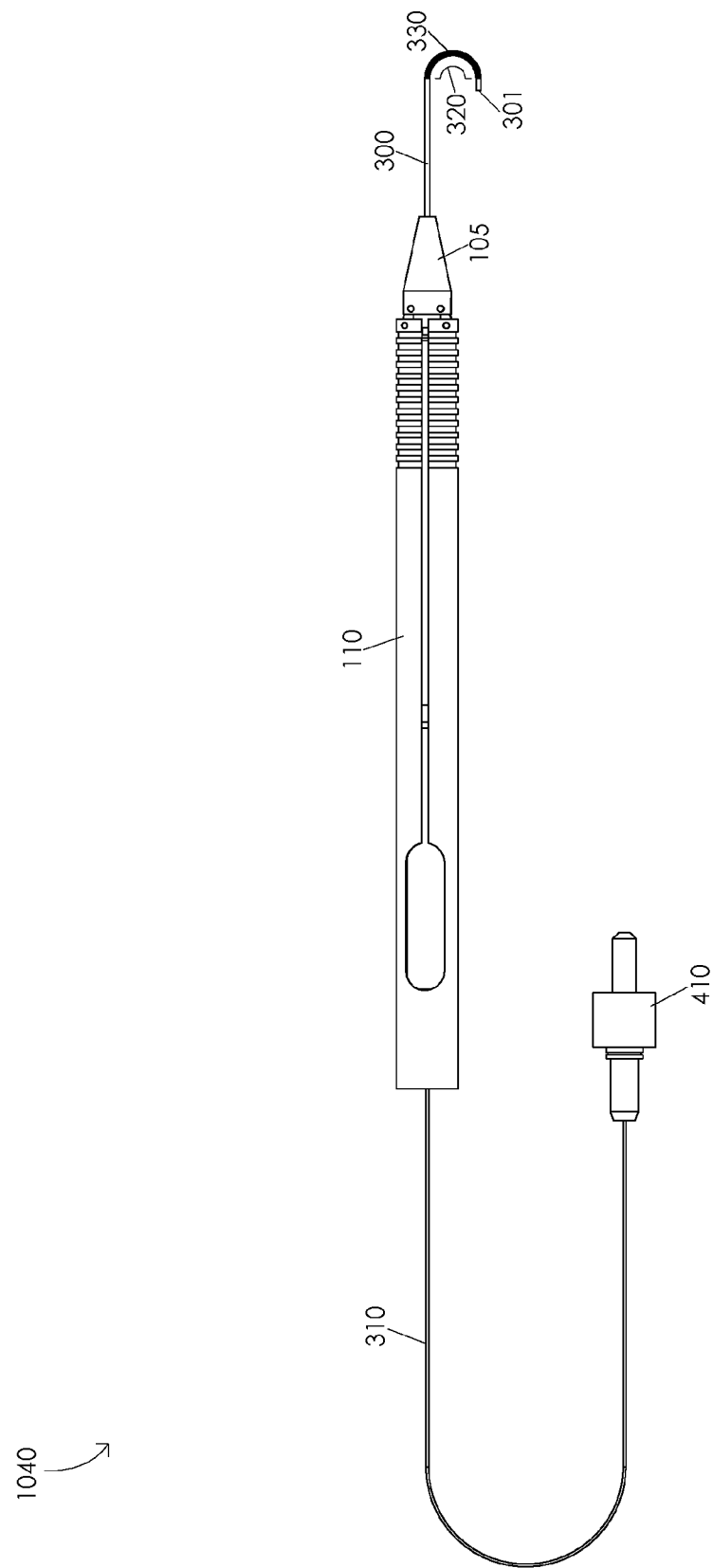

FIG. 10E illustrates an optic fiber in a fourth curved position 1040. In one or more embodiments, a compression of actuation structure 110 may be configured to gradually curve optic fiber 310 from an optic fiber in a third curved position 1030 to an optic fiber in a fourth curved position 1040. Illustratively, a compression of actuation structure 110 may be configured to rotate one or more links 170 about one or more link pins 180. In one or more embodiments, a rotation of one or more links 170 about one or more link pins 180 may be configured to extend nosecone 105 relative to handle proximal end 702. Illustratively, an extension of nosecone 105 relative to handle proximal end 702 may be configured to extend housing tube 300 relative to cable 810. In one or more embodiments, an extension of housing tube 300 relative to cable 810 may be configured to apply a force to a portion of housing tube 300, e.g., a portion of cable 810 fixed to housing tube 300 may be configured to apply a force to housing tube 300. Illustratively, an application of a force to a portion of housing tube 300 may be configured to compress a portion of housing tube 300, e.g., first housing tube portion 320. In one or more embodiments, a compression of a portion of housing tube 300 may be configured to cause housing tube 300 to gradually curve. Illustratively, a gradual curving of housing tube 300 may be configured to gradually curve optic fiber 310, e.g., from an optic fiber in a third curved position 1030 to an optic fiber in a fourth curved position 1040. In one or more embodiments, a line tangent to optic fiber distal end 311 may be parallel to a line tangent to housing tube proximal end 302, e.g., when optic fiber 310 comprises an optic fiber in a fourth curved position 1040.

In one or more embodiments, one or more properties of a steerable laser probe may be adjusted to attain one or more desired steerable laser probe features. Illustratively, a length that housing tube distal end 301 extends from nosecone distal end 106 may be adjusted to vary an amount of compression of actuation structure 110 configured to curve housing tube 300 to a particular curved position. In one or more embodiments, a stiffness of first housing tube portion 320 or a stiffness of second housing tube portion 330 may be adjusted to vary an amount of compression of actuation structure 110 configured to curve housing tube 300 to a particular curved position. Illustratively, a material comprising first housing tube portion 320 or a material comprising second housing tube portion 330 may be adjusted to vary an amount of compression of actuation structure 110 configured to curve housing tube 300 to a particular curved position.

In one or more embodiments, a number of apertures in housing tube 300 may be adjusted to vary an amount of compression of actuation structure 110 configured to curve housing tube 300 to a particular curved position. Illustratively, a location of one or more apertures in housing tube 300 may be adjusted to vary an amount of compression of actuation structure 110 configured to curve housing tube 300 to a particular curved position. In one or more embodiments, a geometry of one or more apertures in housing tube 300 may be adjusted to vary an amount of compression of actuation structure 110 configured to curve housing tube 300 to a particular curved position. Illustratively, a geometry of one or more apertures in housing tube 300 may be uniform, e.g., each aperture of the one or more apertures may have a same geometry. In one or more embodiments, a geometry of one or more apertures in housing tube 300 may be non-uniform, e.g., a first aperture in housing tube 300 may have a first geometry and a second aperture in housing tube 300 may have a second geometry. Illustratively, a geometry or location of one or more apertures in housing tube 300 may be optimized to evenly distribute an applied force. For example, a geometry or location of one or more apertures in housing tube 300 may be optimized to evenly distribute a force applied to first housing tube portion 320.

Illustratively, a stiffness of first housing tube portion 320 or a stiffness of second housing tube portion 330 may be adjusted to vary a bend radius of housing tube 300. In one or more embodiments, a stiffness of first housing tube portion 320 or a stiffness of second housing tube portion 330 may be adjusted to vary a radius of curvature of housing tube 300, e.g., when housing tube 300 is in a particular curved position. Illustratively, a number of apertures in housing tube 300 may be adjusted to vary a bend radius of housing tube 300. In one or more embodiments, a number of apertures in housing tube 300 may be adjusted to vary a radius of curvature of housing tube 300, e.g., when housing tube 300 is in a particular curved position. Illustratively, a location or a geometry of one or more apertures in housing tube 300 may be adjusted to vary a bend radius of housing tube 300. In one or more embodiments, a location or a geometry of one or more apertures in housing tube 300 may be adjusted to vary a radius of curvature of housing tube 300, e.g., when housing tube 300 is in a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

In one or more embodiments, a location wherein cable 810 may be fixed to housing tube 300 may be adjusted to vary an amount of compression of actuation structure 110 configured to curve housing tube 300 to a particular curved position. For example, a portion of cable 810 may be fixed to an outer portion of housing tube 300. Illustratively, cable 810 may be fixed to housing tube 300 at a plurality of fixation points, e.g., to vary one or more properties of a steerable laser probe. In one or more embodiments, a length of cable 810 may be adjusted to vary an amount of compression of actuation structure 110 configured to curve housing tube 300 to a particular curved position. Illustratively, a steerable laser probe may comprise one or more redundant cables 810. In one or more embodiments, one or more redundant cables 810 may be configured to maintain a particular curved position of housing tube 300, e.g., in the event that cable 810 breaks or fails. Illustratively, one or more redundant cables 810 may be configured to maintain a particular curved position of housing tube 300, e.g., in the event that a cable 810 fixation means fails. In one or more embodiments, one or more redundant cables 810 may be configured to maintain a particular curved position of housing tube 300, e.g., in the event that cable 810 is no longer configured to maintain the particular curved position of housing tube 300. Illustratively, one or more redundant cables 810 may be configured to maintain a particular curved position of housing tube 300 wherein cable 810 is also configured to maintain the particular curved position of housing tube 300.

In one or more embodiments, housing tube 300 may comprise an access window configured to allow access to a portion cable 810. Illustratively, cable 810 may be fixed to a portion of housing tube 300, e.g., by looping a portion of cable 810 through an aperture in housing tube 300. In one or more embodiments, cable 810 may be fixed to a portion of housing tube 300, e.g., by a purely mechanical means. For example, cable 810 may be fixed to a portion of housing tube 300 in a manner other than by an adhesive, a weld, etc. Illustratively, cable 810 may be fixed to a portion of housing tube 300 wherein a portion of cable 810 is configured to fail at a first applied failure force and a fixation means that fixes a portion of cable 810 to a portion of housing tube 300 is configured to fail at a second applied failure force. In one or more embodiments, the second applied failure force may be greater than the first applied failure force.

Illustratively, a steerable laser probe may be configured to indicate, e.g., to a surgeon, a direction that optic fiber 310 may curve, e.g., due to a compression of actuation structure 110. In one or more embodiments, a portion of a steerable laser probe, e.g., handle 700, may be marked in a manner configured to indicate a direction that optic fiber 310 may curve. For example, a portion of housing tube 300 may comprise a mark configured to indicate a direction that optic fiber 310 may curve. Illustratively, housing tube 300 may comprise a slight curve, e.g., a curve less than 7.5 degrees, when actuation structure 110 is fully decompressed. In one or more embodiments, housing tube 300 may comprise a slight curve configured to indicate a direction that optic fiber 310 may curve, e.g., due to a compression of actuation structure 110.

Illustratively, a steerable laser probe may comprise an actuation structure 110, a nosecone 105 fixed to actuation structure 110 by one or more links 170 and one or more link pins 180, a housing tube 300, an optic fiber 310, and a cable 810. In one or more embodiments, a compression of actuation structure 110 may be configured to extend nosecone 105 relative to actuation structure proximal end 112. Illustratively, an extension of nosecone 105 relative to actuation structure proximal end 112 may be configured to extend housing tube 300 relative to cable 810. In one or more embodiments, an extension of housing tube 300 relative to cable 810 may be configured to apply a force to housing tube 300. Illustratively an application of a force to housing tube 300 may be configured to compress a portion of housing tube 300. In one or more embodiments, a compression of a portion of housing tube 300 may cause housing tube 300 to gradually curve. Illustratively, a gradual curving of housing tube 300 may be configured to gradually curve optic fiber 310.

Figure 11A:
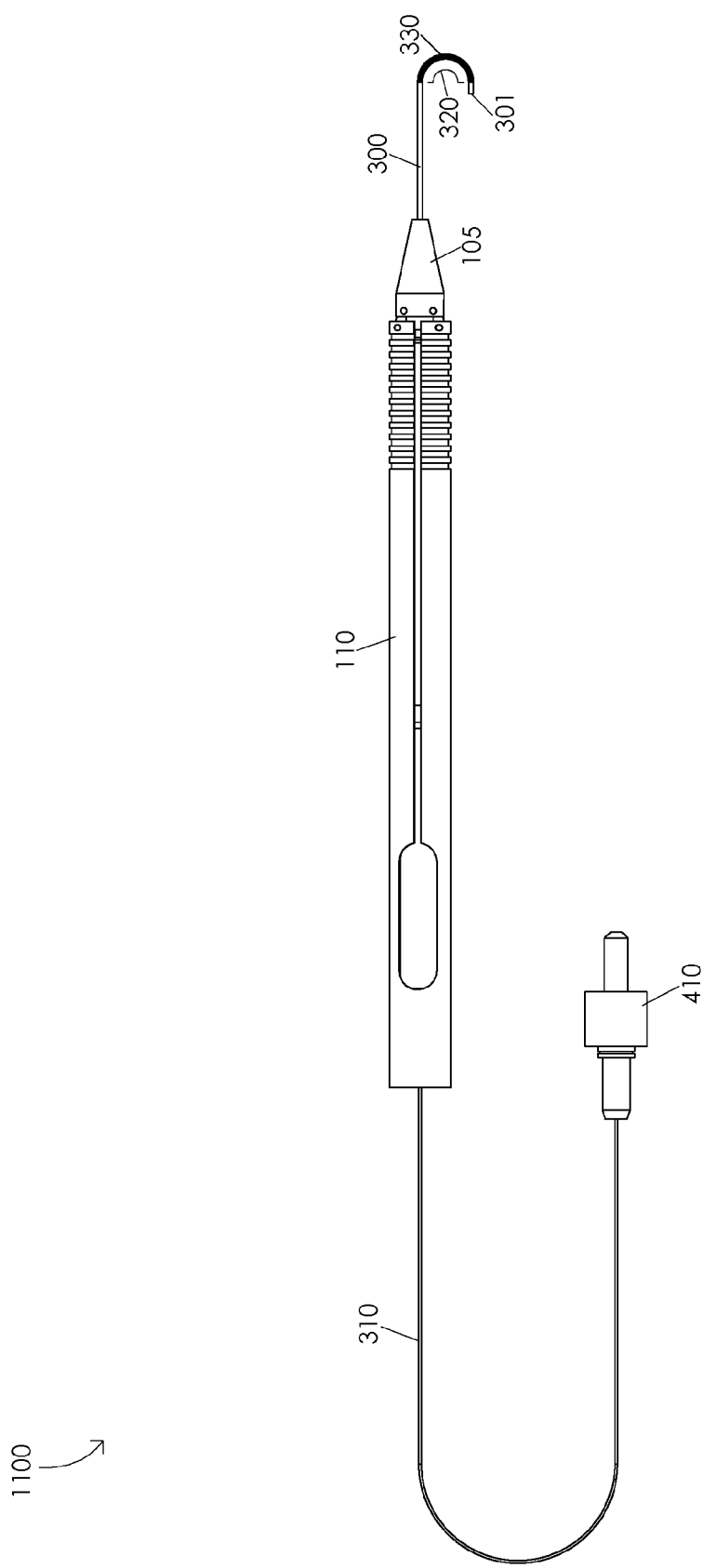
FIGS. 11A, 11B, 11C, 11D, and 11E are schematic diagrams illustrating a gradual straightening of an optic fiber.

FIGS. 11A, 11B, 11C, 11D, and 11E are schematic diagrams illustrating a gradual straightening of an optic fiber 310. FIG. 11A illustrates a fully curved optic fiber 1100. In one or more embodiments, optic fiber 310 may comprise a fully curved optic fiber 1100, e.g., when housing tube 300 is fully extended relative to cable 810. Illustratively, optic fiber 310 may comprise a fully curved optic fiber 1100, e.g., when actuation structure 110 is fully compressed. In one or more embodiments, optic fiber 310 may comprise a fully curved optic fiber 1100, e.g., when nosecone 105 is fully extended relative to handle proximal end 702. For example, optic fiber 310 may comprise a fully curved optic fiber 1100, e.g., when first housing tube portion 320 is fully compressed. Illustratively, a line tangent to optic fiber distal end 311 may be parallel to a line tangent to housing tube proximal end 302, e.g., when optic fiber 310 comprises a fully curved optic fiber 1100.

Figure 11B:
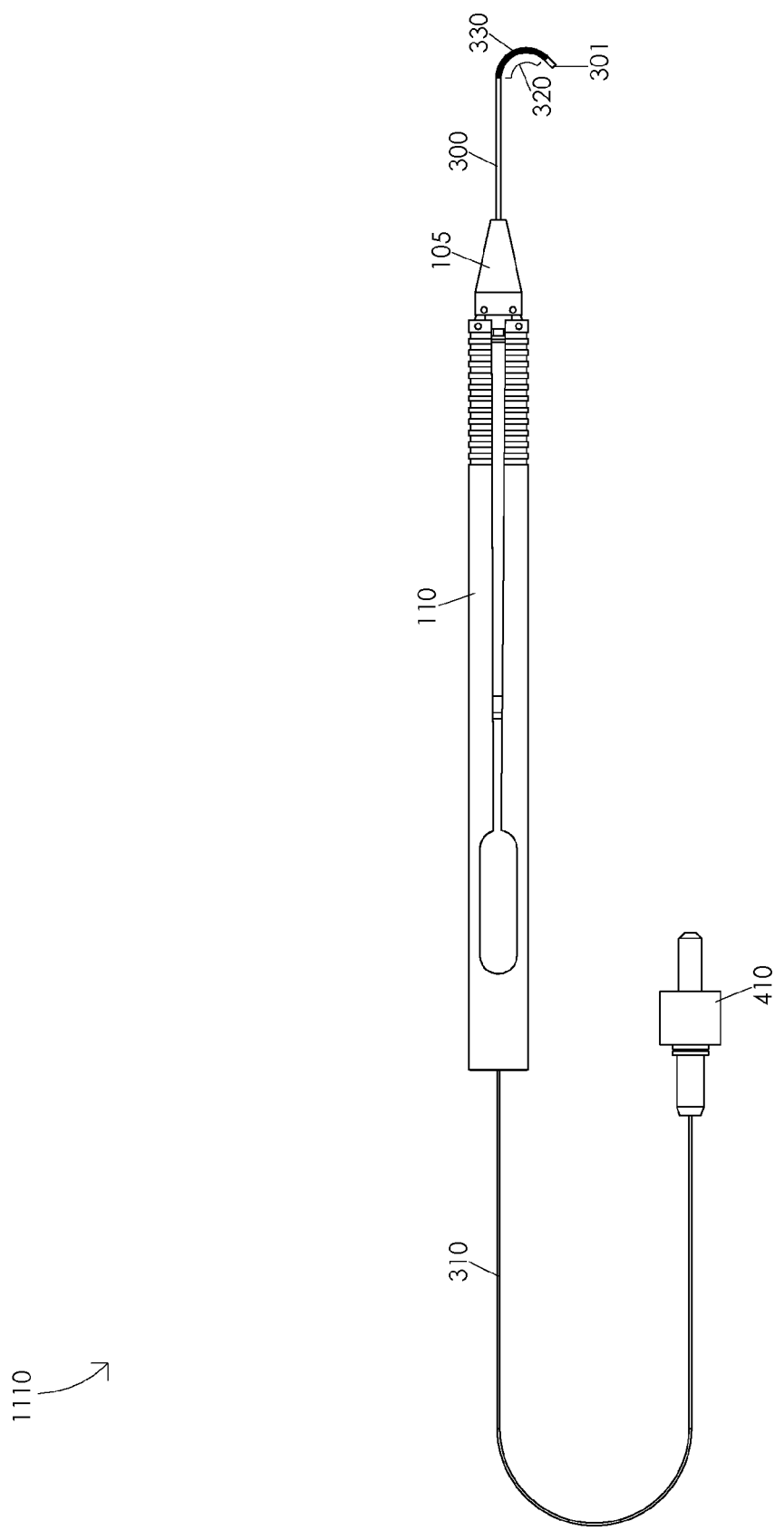

FIG. 11B illustrates an optic fiber in a first partially straightened position 1110. In one or more embodiments, a decompression of actuation structure 110 may be configured to gradually straighten optic fiber 310 from a fully curved optic fiber 1100 to an optic fiber in a first partially straightened position 1110. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 702. Illustratively, a retraction of nosecone 105 relative to handle proximal end 702 may be configured to retract housing tube 300 relative to cable 810. In one or more embodiments, a retraction of housing tube 300 relative to cable 810 may be configured to reduce a force applied to a portion of housing tube 300, e.g., a portion of cable 810 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from a fully curved optic fiber 1100 to an optic fiber in a first partially straightened position 1110. In one or more embodiments, a line tangent to optic fiber distal end 311 may intersect a line tangent to housing tube proximal end 302 at a first partially straightened angle, e.g., when optic fiber 310 comprises an optic fiber in a first partially straightened position 1110. Illustratively, the first partially straightened angle may comprise any angle less than 180 degrees. For example, the first partially straightened angle may comprise a 135 degree angle.

Figure 11C:
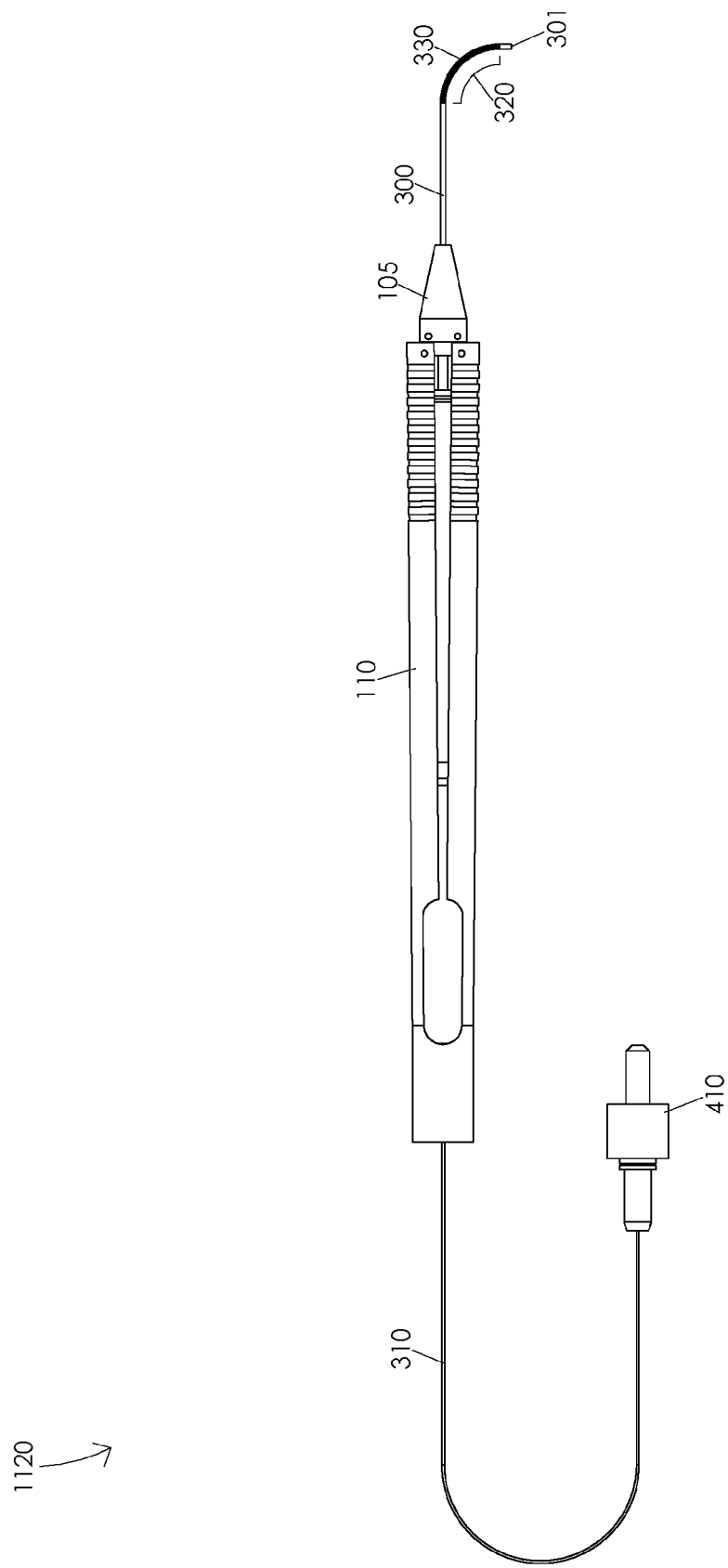

FIG. 11C illustrates an optic fiber in a second partially straightened position 1120. In one or more embodiments, a decompression of actuation structure 110 may be configured to gradually straighten optic fiber 310 from an optic fiber in a first partially straightened position 1110 to an optic fiber in a second partially straightened position 1120. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 702. Illustratively, a retraction of nosecone 105 relative to handle proximal end 702 may be configured to retract housing tube 300 relative to cable 810. In one or more embodiments, a retraction of housing tube 300 relative to cable 810 may be configured to reduce a force applied to a portion of housing tube 300, e.g., a portion of cable 810 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a first partially straightened position 1110 to an optic fiber in a second partially straightened position 1120. In one or more embodiments, a line tangent to optic fiber distal end 311 may intersect a line tangent to housing tube proximal end 302 at a second partially straightened angle, e.g., when optic fiber 310 comprises an optic fiber in a second partially straightened position 1120. Illustratively, the second partially straightened angle may comprise any angle less than the first partially straightened angle. For example, the second partially straightened angle may comprise a 90 degree angle.

Figure 11D:
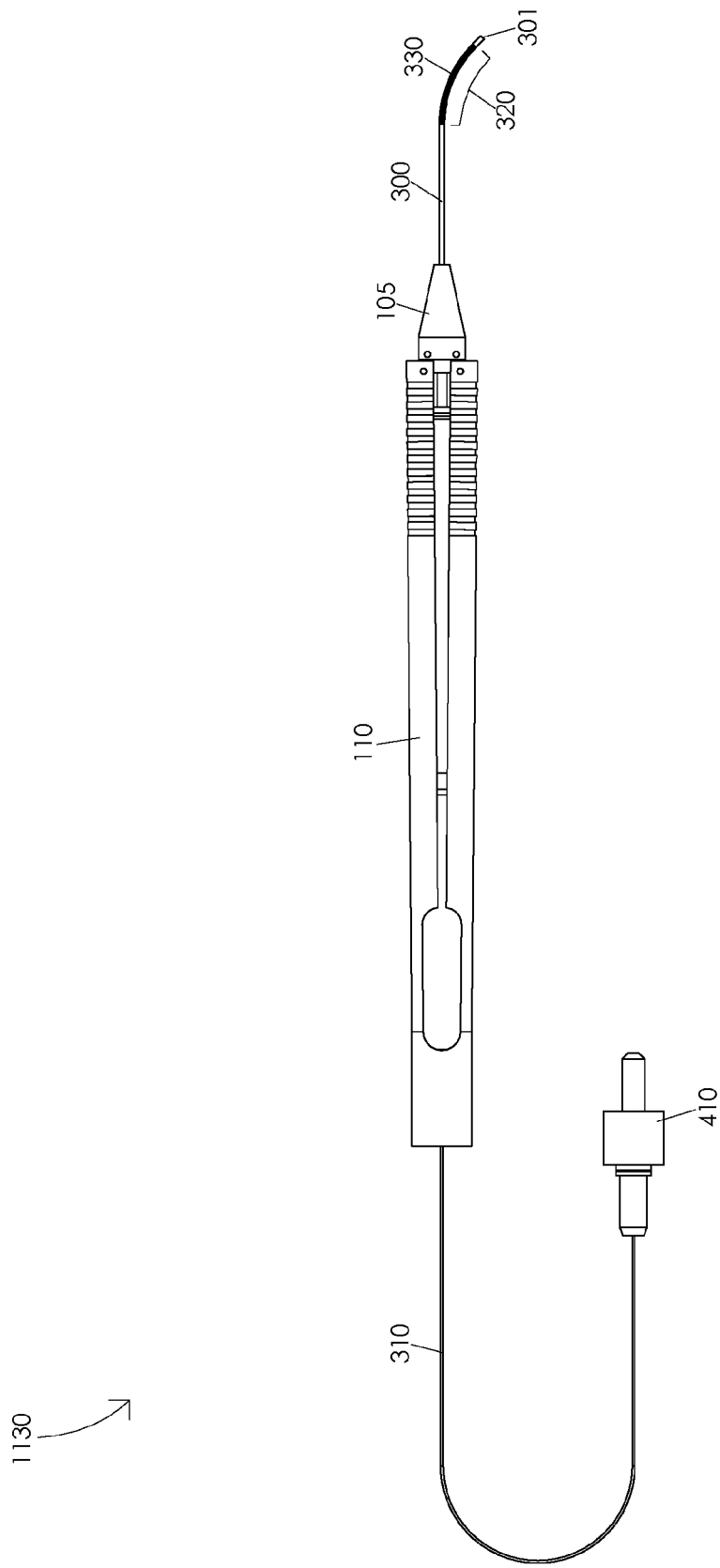

FIG. 11D illustrates an optic fiber in a third partially straightened position 1130. In one or more embodiments, a decompression of actuation structure 110 may be configured to gradually straighten optic fiber 310 from an optic fiber in a second partially straightened position 1120 to an optic fiber in a third partially straightened position 1130. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 702. Illustratively, a retraction of nosecone 105 relative to handle proximal end 702 may be configured to retract housing tube 300 relative to cable 810. In one or more embodiments, a retraction of housing tube 300 relative to cable 810 may be configured to reduce a force applied to a portion of housing tube 300, e.g., a portion of cable 810 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a second partially straightened position 1120 to an optic fiber in a third partially straightened position 1130. In one or more embodiments, a line tangent to optic fiber distal end 311 may intersect a line tangent to housing tube proximal end 302 at a third partially straightened angle, e.g., when optic fiber 310 comprises an optic fiber in a third partially straightened position 1130. Illustratively, the third partially straightened angle may comprise any angle less than the second partially straightened angle. For example, the third partially straightened angle may comprise a 45 degree angle.

Figure 11E:
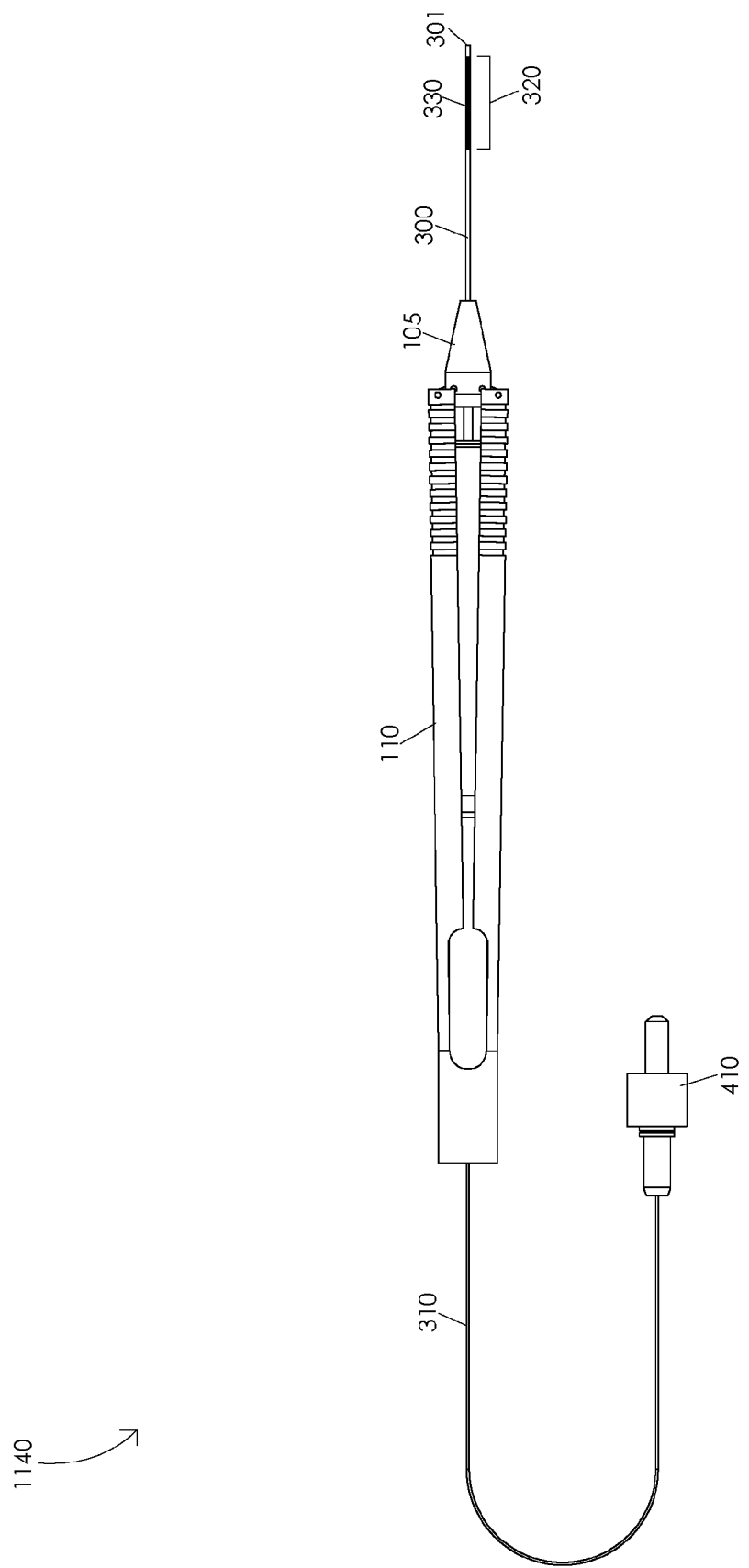

FIG. 11E illustrates an optic fiber in a fully straightened position 1140. In one or more embodiments, a decompression of actuation structure 110 may be configured to gradually straighten optic fiber 310 from an optic fiber in a third partially straightened position 1130 to an optic fiber in a fully straightened position 1140. Illustratively, a decompression of actuation structure 110 may be configured to rotate one or more links 170 about one or more link pins 180. In one or more embodiments, a rotation of one or more links 170 about one or more link pins 180 may be configured to retract nosecone 105 relative to handle proximal end 702. Illustratively, a retraction of nosecone 105 relative to handle proximal end 702 may be configured to retract housing tube 300 relative to cable 810. In one or more embodiments, a retraction of housing tube 300 relative to cable 810 may be configured to reduce a force applied to a portion of housing tube 300, e.g., a portion of cable 810 fixed to housing tube 300 may be configured to reduce a force applied to housing tube 300. Illustratively, a reduction of a force applied to a portion of housing tube 300 may be configured to decompress a portion of housing tube 300, e.g., first housing tube portion 320. In one or more embodiments, a decompression of a portion of housing tube 300 may be configured to cause housing tube 300 to gradually straighten. Illustratively, a gradual straightening of housing tube 300 may be configured to gradually straighten optic fiber 310, e.g., from an optic fiber in a third partially straightened position 1130 to an optic fiber in a fully straightened position 1140. In one or more embodiments, a line tangent to optic fiber distal end 311 may be parallel to a line tangent to housing tube proximal end 302, e.g., when optic fiber 310 comprises an optic fiber in a fully straightened position 1140.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 700 to orient housing tube 300 in an orientation configured to cause a curvature of housing tube 300 within the particular transverse plane of the inner eye and varying an amount of compression of actuation structure 110. Illustratively, a surgeon may aim optic fiber distal end 311 at any target within a particular sagittal plane of the inner eye by, e.g., rotating handle 700 to orient housing tube 300 in an orientation configured to cause a curvature of housing tube 300 within the particular sagittal plane of the inner eye and varying an amount of compression of actuation structure 110. In one or more embodiments, a surgeon may aim optic fiber distal end 311 at any target within a particular frontal plane of the inner eye by, e.g., varying an amount of actuation of actuation structure 110 to orient a line tangent to optic fiber distal end 311 wherein the line tangent to optic fiber distal end 311 is within the particular frontal plane of the inner eye and rotating handle 700. Illustratively, a surgeon may aim optic fiber distal end 311 at any target located outside of the particular transverse plane, the particular sagittal plane, and the particular frontal plane of the inner eye, e.g., by varying a rotational orientation of handle 700 and varying an amount of compression of actuation structure 110. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   an actuation structure of a handle having an actuation structure distal end and an actuation structure proximal end wherein the handle has a handle distal end and a handle proximal end;
   a nosecone having a housing tube housing;
   a first link wherein the first link is fixed to the actuation structure by a first link pin and wherein the first link is fixed to the nosecone by a second link pin;
   a first spacer disposed over the first link pin, the first spacer configured to prevent movement of the first link relative to the first link pin;
   a second spacer disposed over the second link pin, the second spacer configured to prevent movement of the first link relative to the second link pin;
   a second link wherein the second link is fixed to the actuation structure by a third link pin and wherein the second link is fixed to the nosecone by a fourth link pin and wherein a rotation of the first link about the first link pin and the second link pin and a rotation of the second link about the third link pin and the fourth link pin is configured to extend the nosecone relative to the handle proximal end;
   a single housing tube having a housing tube distal end and a housing tube proximal end wherein the housing tube proximal end is disposed within the housing tube housing and wherein the housing tube proximal end is fixed within the housing tube housing;
   a first housing tube portion of the housing tube having a first inner diameter, the first housing tube portion having a first stiffness;
   a second housing tube portion of the housing tube having a second inner diameter, the second housing tube portion having a second stiffness wherein the second stiffness is greater than the first stiffness and wherein the first inner diameter is larger than the second inner diameter;

a cable having a cable distal end and a cable proximal end, the cable disposed in a cable housing and the housing tube wherein the cable is fixed in the cable housing and wherein the cable is fixed to a portion of the housing tube; and an optic fiber having an optic fiber distal end and an optic fiber proximal end, the optic fiber disposed in the actuation structure and the housing tube wherein the optic fiber distal end is adjacent to the housing tube distal end and wherein a portion of the optic fiber is fixed to the housing tube.

2. The instrument of claim 1 wherein a compression of the actuation structure is configured to curve the optic fiber.

3. The instrument of claim 2 wherein the compression of the actuation structure is configured to curve the optic fiber at least 45 degrees relative to the housing tube proximal end.

4. The instrument of claim 3 wherein the compression of the actuation structure is configured to curve the optic fiber at least 90 degrees relative to the housing tube proximal end.

5. The instrument of claim 1 wherein a compression of the actuation structure is configured to curve the housing tube.

6. The instrument of claim 5 wherein the compression of the actuation structure is configured to curve the housing tube at least 45 degrees.

7. The instrument of claim 6 wherein the compression of the actuation structure is configured to curve the housing tube at least 90 degrees.

8. The instrument of claim 1 further comprising:
a piston having a piston distal end and a piston proximal end.

9. The instrument of claim 1 further comprising:
an inner hypodermic tube having an inner hypodermic tube distal end and an inner hypodermic tube proximal end.

10. The instrument of claim 1 further comprising:
an actuation guide having an actuation guide distal end and an actuation guide proximal end.

11. The instrument of claim 1 further comprising:
an outer sleeve having an outer sleeve distal end and an outer sleeve proximal end.

12. The instrument of claim 1 further comprising:
a redundant cable having a redundant cable distal end and a redundant cable proximal end, the redundant cable configured to maintain a particular curved position of the housing tube if the cable fails to maintain the particular curved position of the housing tube.

13. An instrument comprising:
an actuation structure of a handle having an actuation structure distal end and an actuation structure proximal end wherein the handle has a handle distal end and a handle proximal end;
a nosecone having a housing tube housing;
a first link wherein the first link is fixed to the actuation structure by a first link pin and wherein the first link is fixed to the nosecone by a second link pin;
a first spacer disposed over the first link pin, the first spacer configured to prevent movement of the first link relative to the first link pin;
a second spacer disposed over the second link pin, the second spacer configured to prevent movement of the first link relative to the second link pin;
a second link wherein the second link is fixed to the actuation structure by a third link pin and wherein the second link is fixed to the nosecone by a fourth link pin and wherein a rotation of the first link about the first link pin and the second link pin and a rotation of the second link about the third link pin and the fourth link pin is configured to extend the nosecone relative to the handle proximal end;
a single housing tube having a housing tube distal end and a housing tube proximal end wherein the housing tube proximal end is disposed within the housing tube housing and wherein the housing tube proximal end is fixed within the housing tube housing;
a first housing tube portion of the housing tube having a first inner diameter, the first housing tube portion having a first stiffness;
a second housing tube portion of the housing tube having a second inner diameter, the second housing tube portion having a second stiffness wherein the second stiffness is greater than the first stiffness and wherein the first inner diameter is larger than the second inner diameter;
a cable having a cable distal end and a cable proximal end, the cable disposed in a cable housing and the housing tube wherein the cable is fixed in the cable housing and wherein the cable is fixed to a portion of the housing tube;
a redundant cable having a redundant cable distal end and a redundant cable proximal end; and
an optic fiber having an optic fiber distal end and an optic fiber proximal end, the optic fiber disposed in the actuation structure and the housing tube wherein the optic fiber distal end is adjacent to the housing tube distal end and wherein a portion of the optic fiber is fixed to the housing tube.

14. The instrument of claim 13 wherein a compression of the actuation structure is configured to curve the optic fiber.

15. The instrument of claim 13 wherein a compression of the actuation structure is configured to curve the housing tube.

16. The instrument of claim 13 wherein a decompression of the actuation structure is configured to straighten the optic fiber.

17. The instrument of claim 13 wherein a decompression of the actuation structure is configured to straighten the housing tube.

18. The instrument of claim 13 further comprising:
a piston having a piston distal end and a piston proximal end; and
an inner hypodermic tube having an inner hypodermic tube distal end and an inner hypodermic tube proximal end wherein the inner hypodermic tube proximal end is disposed in the piston.

19. The instrument of claim 13 further comprising:
an outer sleeve having an outer sleeve distal end and an outer sleeve proximal end.

20. The instrument of claim 19 further comprising:
an actuation guide having an actuation guide distal end and an actuation guide proximal end wherein the actuation guide is disposed in the outer sleeve.

* * * * *